(12) United States Patent
Inouye et al.

(10) Patent No.: US 10,184,116 B2
(45) Date of Patent: Jan. 22, 2019

(54) **CHIMERIC GENES FOR THE CATALYTIC PROTEIN OF *OPLOPHORUS* LUCIFERASE AND USE THEREOF**

(71) Applicant: JNC CORPORATION, Tokyo (JP)

(72) Inventors: Satoshi Inouye, Kanagawa (JP); Junichi Sato, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 479 days.

(21) Appl. No.: 14/641,908

(22) Filed: Mar. 9, 2015

(65) Prior Publication Data

US 2015/0259652 A1 Sep. 17, 2015

(30) Foreign Application Priority Data

Mar. 11, 2014 (JP) .................................. 2014-047379

(51) Int. Cl.
*C12N 9/02* (2006.01)
*C12Q 1/66* (2006.01)

(52) U.S. Cl.
CPC ............. *C12N 9/0069* (2013.01); *C12Q 1/66* (2013.01); *C12Y 113/12013* (2013.01); *G01N 2333/90241* (2013.01)

(58) Field of Classification Search
CPC . C12N 1/20; C12N 5/00; C12N 15/00; C12N 9/02; C12P 21/04; C12Q 1/66
See application file for complete search history.

(56) References Cited

U.S. PATENT DOCUMENTS

| | | | | |
|---|---|---|---|---|
| 8,557,970 B2 * | 10/2013 | Encell | ...................... | C12Q 1/66 435/189 |
| 8,669,103 B2 * | 3/2014 | Binkowski | ........... | C07D 487/04 435/252.3 |
| 2002/0102687 A1 | 8/2002 | Inouye | | |
| 2004/0002127 A1 | 1/2004 | Inouye | | |
| 2010/0281552 A1 | 11/2010 | Encell et al. | | |
| 2012/0117667 A1 | 5/2012 | Klaubert et al. | | |

FOREIGN PATENT DOCUMENTS

| | | |
|---|---|---|
| JP | 4613441 B2 | 1/2011 |
| JP | 2012-525819 A | 10/2012 |
| WO | WO-2010/127368 A1 | 11/2010 |

OTHER PUBLICATIONS

Osamu Shimomura, et al., "Properties and Reaction Mechanism of the Bioluminescence System of the Deep-Sea Shrimp *Oplophorus gracilorostris+*," Biochemistry vol. 17, No. 6, 1978, pp. 994-998.
Satoshi Inouye, et al., "Secretional luciferase of the luminous shrimp *Oplophorus gracilirostris*: cDNA cloning of a novel imidazopyrazinone luciferase[1] ," FEBS Letters 481 (2000), pp. 19-25.
Satoshi Inouye, et al., "Overexpression, purification and characterization of the catalytic component of *Oplophorus* luciferase in the deep-sea shrimp, *Oplophorus gracilirostris*," Protein Expression and Purification 56 (2007), pp. 261-268.
Mary P. Hall, et al., "Engineered Luciferase Reporter from a Deep Sea Shrimp Utilizing a Novel Imidazopyrazinone Substrate," ACS Chemical Biology 7 (2012) pp. 1848-1857.
Satoshi Inouye, et al., "C6-Deoxy coelenterazine analogues as an efficient substrate for glow luminescence reaction of nanoKAZ: The mutated catalytic 19 kDa component of *Oplophorus* luciferase," Biochemical and Biophysical Research Communications 437 (2013) pp. 23-28.
Satoshi Inouye, et al., "Expression, purification and luminescence properties of coelenterazine-utilizing luciferases from *Renilla*, *Oplophorus* and *Gaussia*: Comparison of substrate specificity for C2-modified coelenterazines," Protein Expression and Purification 88 (2013) pp. 150-156.
GB 1503811.0—Search Report mailed Dec. 10, 2015.
Inouye et al., "Luminescence enhancement of the catalytic 19 kDa protein (KAZ) of Oplophorus luciferase by three amino acid substitutions", Biochem Biophys Res Commun., Feb. 28, 2014; 445(1):157-62 (Epub Jan. 31, 2014).

* cited by examiner

*Primary Examiner* — Maryam Monshipouri
(74) *Attorney, Agent, or Firm* — Drinker Biddle & Reath LLP

(57) ABSTRACT

A novel luciferase that distinct from conventional luciferase has been desired. A luciferase mutant comprising the amino acid sequence of SEQ ID NO: 2 substituted at tyrosine at the position of 138, and at least 3 positions selected from the group consisting of isoleucine at the position of 90, proline at the position of 115, glutamine at the position of 124, and asparagine at the position of 166.

19 Claims, 1 Drawing Sheet
(1 of 1 Drawing Sheet(s) Filed in Color)
Specification includes a Sequence Listing.

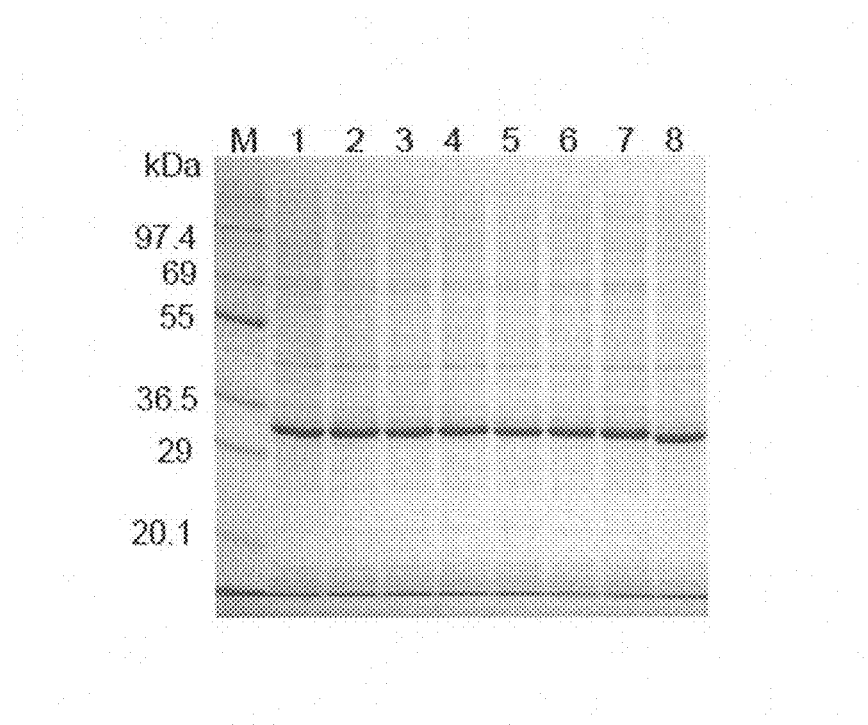

SEQUENCE LISTING

```
<160> NUMBER OF SEQ ID NOS: 34

<210> SEQ ID NO 1
<211> LENGTH: 510
<212> TYPE: DNA
<213> ORGANISM: Oplophorus gracilirostris
<220> FEATURE:
<221> NAME/KEY: CDS
<222> LOCATION: (1)..(507)

<400> SEQUENCE: 1 ttt acg ttg gca gat ttc gtt gga gac tgg caa cag aca gct gga tac        48
Phe Thr Leu Ala Asp Phe Val Gly Asp Trp Gln Gln Thr Ala Gly Tyr
  1               5                  10                  15 aac caa gat caa gtg tta gaa caa gga gga ttg tct agt ctg ttc caa        96
Asn Gln Asp Gln Val Leu Glu Gln Gly Gly Leu Ser Ser Leu Phe Gln
             20                  25                  30 gcc ctg gga gtg tca gtc acg ccc ata cag aaa gtt gta ctg tct ggg       144
Ala Leu Gly Val Ser Val Thr Pro Ile Gln Lys Val Val Leu Ser Gly
         35                  40                  45 gag aat ggg tta aaa gct gat att cat gtc ata ata cct tac gag gga       192
Glu Asn Gly Leu Lys Ala Asp Ile His Val Ile Ile Pro Tyr Glu Gly
     50                  55                  60 ctc agt ggt ttt caa atg ggt cta att gaa atg atc ttc aaa gtt gtt       240
Leu Ser Gly Phe Gln Met Gly Leu Ile Glu Met Ile Phe Lys Val Val
 65                  70                  75                  80 tac ccc gtg gat gat cat cat ttc aag att att ctc cat tat ggt aca       288
Tyr Pro Val Asp Asp His His Phe Lys Ile Ile Leu His Tyr Gly Thr
                 85                  90                  95 ctc gtt att gac ggt gta aca ccc aac atg att gac tac ttt gga aga       336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act       384
Pro Tyr Pro Gly Ile Ala Val Phe Asp Gly Lys Gln Ile Thr Val Thr
        115                 120                 125 gga act ctg tgg aac ggc aac aag atc tat gat gag agg cta atc aac       432
```

```
                  Gly Thr Leu Trp Asn Gly Asn Lys Ile Tyr Asp Glu Arg Leu Ile Asn
                                  130                 135                 140 cct gat ggt tca ctc ctc ttc aga gtt act atc aat gga gtc acg gga      480
Pro Asp Gly Ser Leu Leu Phe Arg Val Thr Ile Asn Gly Val Thr Gly
145                 150                 155                 160 tgg agg ctt tgc gag aac att ctt gcc taa                              510
Trp Arg Leu Cys Glu Asn Ile Leu Ala
                165
```

```
<210> SEQ ID NO 2
<211> LENGTH: 169
<212> TYPE: PRT
<213> ORGANISM: Oplophorus gracilirostris

<400> SEQUENCE: 2

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
                20                  25                  30

Ala Leu Gly Val Ser Val Thr Pro Ile Gln Lys Val Val Leu Ser Gly
            35                  40                  45

Glu Asn Gly Leu Lys Ala Asp Ile His Val Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

```
<210> SEQ ID NO 3
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(507)

<400> SEQUENCE: 3 ttc acc ctg gag gac ttc gtc ggc gac tgg aga cag acc gcc ggc tac     48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag     96
Asn Leu Asp Gln Val Leu Glu Gln Gly Gly Val Ser Ser Leu Phe Gln
                20                  25                  30 aac ctg ggc gtc agc gtc acc ccc atc cag aga atc gtc ctt agc ggc    144
Asn Leu Gly Val Ser Val Thr Pro Ile Gln Arg Ile Val Leu Ser Gly
            35                  40                  45 gag aac ggc ctg aag atc gac atc cac gtc atc atc ccc tac gag ggc    192
```

```
                Glu Asn Gly Leu Lys Ile Asp Ile His Val Ile Ile Pro Tyr Glu Gly
                 50                  55                  60 ctg agc ggc gac cag atg ggc cag atc gag aag atc ttc aag gtc gtc           240
Leu Ser Gly Asp Gln Met Gly Gln Ile Glu Lys Ile Phe Lys Val Val
 65                  70                  75                  80 tac ccc gtc gac gac cac cac ttc aag gtc atc ctg cac tac ggc acc           288
Tyr Pro Val Asp Asp His His Phe Lys Val Ile Leu His Tyr Gly Thr
                 85                  90                  95 ctg gtc atc gac ggc gtc acc ccc aac atg atc gac tac ttc ggt aga           336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc           384
Pro Tyr Glu Gly Ile Ala Val Phe Asp Gly Lys Lys Ile Thr Val Thr
        115                 120                 125 ggc acc ctg tgg aac ggc aac aag atc atc gac gag aga ctg atc aac           432
Gly Thr Leu Trp Asn Gly Asn Lys Ile Ile Asp Glu Arg Leu Ile Asn
130                 135                 140 ccc gac ggc agc ctg ctg ttc aga gtc acc atc aac ggc gtc acc ggc           480
Pro Asp Gly Ser Leu Leu Phe Arg Val Thr Ile Asn Gly Val Thr Gly
145                 150                 155                 160 tgg aga ctg tgc gag aga atc ctg gcc taa                                   510
Trp Arg Leu Cys Glu Arg Ile Leu Ala
                165

<210> SEQ ID NO 4
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Phe Thr Leu Glu Asp Phe Val Gly Asp Trp Arg Gln Thr Ala Gly Tyr
 1               5                  10                  15

Asn Leu Asp Gln Val Leu Glu Gln Gly Gly Val Ser Ser Leu Phe Gln
                20                  25                  30

Asn Leu Gly Val Ser Val Thr Pro Ile Gln Arg Ile Val Leu Ser Gly
            35                  40                  45

Glu Asn Gly Leu Lys Ile Asp Ile His Val Ile Ile Pro Tyr Glu Gly
 50                  55                  60

Leu Ser Gly Asp Gln Met Gly Gln Ile Glu Lys Ile Phe Lys Val Val
 65                  70                  75                  80

Tyr Pro Val Asp Asp His His Phe Lys Val Ile Leu His Tyr Gly Thr
                 85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165

<210> SEQ ID NO 5
<211> LENGTH: 510
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(507)

<400> SEQUENCE: 5

```
ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa      96
Asn Gln Asp Gln Val Leu Glu Gln Gly Gly Leu Ser Ser Leu Phe Gln
            20                  25                  30 gcc ctg gga gtg tca gtc acg ccc ata cag aaa gtt gta ctg tct ggg     144
Ala Leu Gly Val Ser Val Thr Pro Ile Gln Lys Val Val Leu Ser Gly
        35                  40                  45 gag aat ggg tta aaa gct gat att cat gtc ata ata cct tac gag gga     192
Glu Asn Gly Leu Lys Ala Asp Ile His Val Ile Ile Pro Tyr Glu Gly
    50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtc gac gac cac cac ttc aag gtc atc ctg cac tac ggc acc     288
Tyr Pro Val Asp Asp His His Phe Lys Val Ile Leu His Tyr Gly Thr
                85                  90                  95 ctg gtc atc gac ggc gtc acc ccc aac atg atc gac tac ttc ggt aga     336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc     384
Pro Tyr Glu Gly Ile Ala Val Phe Asp Gly Lys Lys Ile Thr Val Thr
        115                 120                 125 ggc acc ctg tgg aac ggc aac aag atc atc gac gag aga ctg atc aac     432
Gly Thr Leu Trp Asn Gly Asn Lys Ile Ile Asp Glu Arg Leu Ile Asn
    130                 135                 140 ccc gac ggc agc ctg ctg ttc aga gtc acc atc aac ggc gtc acc ggc     480
Pro Asp Gly Ser Leu Leu Phe Arg Val Thr Ile Asn Gly Val Thr Gly
145                 150                 155                 160 tgg aga ctg tgc gag aga atc ctg gcc taa                             510
Trp Arg Leu Cys Glu Arg Ile Leu Ala
                165
```

<210> SEQ ID NO 6
<211> LENGTH: 169
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80
```

```
Tyr Pro Val Asp Asp His His Phe Lys Val Ile Leu His Tyr Gly Thr
             85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165

<210> SEQ ID NO 7
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(507)

<400> SEQUENCE: 7 ttt acg ttg gca gat ttc gtt gga gac tgg caa cag aca gct gga tac     48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa     96
Asn Gln Asp Gln Val Leu Glu Gln Gly Gly Leu Ser Ser Leu Phe Gln
            20                  25                  30 gcc ctg gga gtg tca gtc acg ccc ata cag aaa gtt gta ctg tct ggg    144
Ala Leu Gly Val Ser Val Thr Pro Ile Gln Lys Val Val Leu Ser Gly
        35                  40                  45 gag aat ggg tta aaa gct gat att cat gtc ata ata cct tac gag gga    192
Glu Asn Gly Leu Lys Ala Asp Ile His Val Ile Ile Pro Tyr Glu Gly
    50                  55                  60 ctc agt ggt ttt caa atg ggt cta att gaa atg atc ttc aaa gtt gtt    240
Leu Ser Gly Phe Gln Met Gly Leu Ile Glu Met Ile Phe Lys Val Val
65                  70                  75                  80 tac ccc gtc gac gac cac cac ttc aag att atc ctg cac tac ggc acc    288
Tyr Pro Val Asp Asp His His Phe Lys Ile Ile Leu His Tyr Gly Thr
             85                  90                  95 ctg gtc atc gac ggc gtc acc ccc aac atg atc gac tac ttc ggt aga    336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc    384
Pro Tyr Glu Gly Ile Ala Val Phe Asp Gly Lys Lys Ile Thr Val Thr
        115                 120                 125 ggc acc ctg tgg aac ggc aac aag atc atc gac gag aga ctg atc aac    432
Gly Thr Leu Trp Asn Gly Asn Lys Ile Ile Asp Glu Arg Leu Ile Asn
    130                 135                 140 ccc gac ggc agc ctg ctg ttc aga gtc acc atc aac ggc gtc acc ggc    480
Pro Asp Gly Ser Leu Leu Phe Arg Val Thr Ile Asn Gly Val Thr Gly
145                 150                 155                 160 tgg aga ctg tgc gag aga atc ctg gcc taa                            510
Trp Arg Leu Cys Glu Arg Ile Leu Ala
                165

<210> SEQ ID NO 8
```

-continued

```
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165

<210> SEQ ID NO 9
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(507)

<400> SEQUENCE: 9 ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa      96
Asn Gln Asp Gln Val Leu Glu Gln Gly Gly Leu Ser Ser Leu Phe Gln
            20                  25                  30 gcc ctg gga gtg tca gtc acg ccc ata cag aaa gtt gta ctg tct ggg     144
Ala Leu Gly Val Ser Val Thr Pro Ile Gln Lys Val Val Leu Ser Gly
        35                  40                  45 gag aat ggg tta aaa gct gat att cat gtc ata ata cct tac gag gga     192
Glu Asn Gly Leu Lys Ala Asp Ile His Val Ile Ile Pro Tyr Glu Gly
    50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtc gac gac cac cac ttc aag gtc atc ctg cac tac ggc acc     288
Tyr Pro Val Asp Asp His His Phe Lys Val Ile Leu His Tyr Gly Thr
                85                  90                  95
```

```
ctg gtc atc gac ggc gtc acc ccc aac atg atc gac tac ttc ggt aga      336
Leu Val Ile Asp Gly Val Thr Pro Asn Met Ile Asp Tyr Phe Gly Arg
            100                 105                 110 ccc tac cct ggc atc gcc gtc ttc gac ggc aag aag atc acc gtc acc      384
Pro Tyr Pro Gly Ile Ala Val Phe Asp Gly Lys Lys Ile Thr Val Thr
        115                 120                 125 ggc acc ctg tgg aac ggc aac aag atc atc gac gag aga ctg atc aac      432
Gly Thr Leu Trp Asn Gly Asn Lys Ile Ile Asp Glu Arg Leu Ile Asn
130                 135                 140 ccc gac ggc agc ctg ctg ttc aga gtc acc atc aac ggc gtc acc ggc      480
Pro Asp Gly Ser Leu Leu Phe Arg Val Thr Ile Asn Gly Val Thr Gly
145                 150                 155                 160 tgg aga ctg tgc gag aga atc ctg gcc taa                              510
Trp Arg Leu Cys Glu Arg Ile Leu Ala
                165
```

<210> SEQ ID NO 10
<211> LENGTH: 169
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165
```

<210> SEQ ID NO 11
<211> LENGTH: 510
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(507)

<400> SEQUENCE: 11

| | | |
|---|---|---|
| ttt acg ttg gca gat ttc gtt gga gac tgg caa cag aca gct gga tac<br>Phe Thr Leu Ala Asp Phe Val Gly Asp Trp Gln Gln Thr Ala Gly Tyr<br>1               5                   10                  15 | | 48 |
| aac caa gat caa gtg tta gaa caa gga gga ttg tct agt ctg ttc caa<br>Asn Gln Asp Gln Val Leu Glu Gln Gly Gly Leu Ser Ser Leu Phe Gln<br>            20                  25                  30 | | 96 |
| gcc ctg gga gtg tca gtc acg ccc ata cag aaa gtt gta ctg tct ggg<br>Ala Leu Gly Val Ser Val Thr Pro Ile Gln Lys Val Val Leu Ser Gly<br>        35                  40                  45 | | 144 |
| gag aat ggg tta aaa gct gat att cat gtc ata ata cct tac gag gga<br>Glu Asn Gly Leu Lys Ala Asp Ile His Val Ile Ile Pro Tyr Glu Gly<br>    50                  55                  60 | | 192 |
| ctc agt ggt ttt caa atg ggt cta att gaa atg atc ttc aaa gtt gtt<br>Leu Ser Gly Phe Gln Met Gly Leu Ile Glu Met Ile Phe Lys Val Val<br>65                  70                  75                  80 | | 240 |
| tac ccc gtc gac gac cac cac ttc aag gtc atc ctg cac tac ggc acc<br>Tyr Pro Val Asp Asp His His Phe Lys Val Ile Leu His Tyr Gly Thr<br>                85                  90                  95 | | 288 |
| ctg gtc atc gac ggc gtc acc ccc aac atg atc gac tac ttc ggt aga<br>Leu Val Ile Asp Gly Val Thr Pro Asn Met Ile Asp Tyr Phe Gly Arg<br>            100                 105                 110 | | 336 |
| ccc tac gag ggc atc gcc gtc ttc gac ggc aag cag atc acc gtc acc<br>Pro Tyr Glu Gly Ile Ala Val Phe Asp Gly Lys Gln Ile Thr Val Thr<br>        115                 120                 125 | | 384 |
| ggc acc ctg tgg aac ggc aac aag atc atc gac gag aga ctg atc aac<br>Gly Thr Leu Trp Asn Gly Asn Lys Ile Ile Asp Glu Arg Leu Ile Asn<br>    130                 135                 140 | | 432 |
| ccc gac ggc agc ctg ctg ttc aga gtc acc atc aac ggc gtc acc ggc<br>Pro Asp Gly Ser Leu Leu Phe Arg Val Thr Ile Asn Gly Val Thr Gly<br>145                 150                 155                 160 | | 480 |
| tgg aga ctg tgc gag aga atc ctg gcc taa<br>Trp Arg Leu Cys Glu Arg Ile Leu Ala<br>                165 | | 510 |

<210> SEQ ID NO 12
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Gln Ile Thr Val Thr
        115                 120                 125

```
Gly Thr Leu Trp Asn Gly Asn Lys Ile Ile Asp Glu Arg Leu Ile Asn
            130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165
```

<210> SEQ ID NO 13
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(507)

<400> SEQUENCE: 13

```
ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa      96
Asn Gln Asp Gln Val Leu Glu Gln Gly Gly Leu Ser Ser Leu Phe Gln
                20                  25                  30 gcc ctg gga gtg tca gtc acg ccc ata cag aaa gtt gta ctg tct ggg     144
Ala Leu Gly Val Ser Val Thr Pro Ile Gln Lys Val Val Leu Ser Gly
            35                  40                  45 gag aat ggg tta aaa gct gat att cat gtc ata ata cct tac gag gga     192
Glu Asn Gly Leu Lys Ala Asp Ile His Val Ile Ile Pro Tyr Glu Gly
        50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtc gac gac cac cac ttc aag gtc atc ctg cac tac ggc acc     288
Tyr Pro Val Asp Asp His His Phe Lys Val Ile Leu His Tyr Gly Thr
                85                  90                  95 ctg gtc atc gac ggc gtc acc ccc aac atg atc gac tac ttc ggt aga     336
Leu Val Ile Asp Gly Val Thr Pro Asn Met Ile Asp Tyr Phe Gly Arg
            100                 105                 110 ccc tac gag ggc atc gcc gtc ttc gac ggc aag aag atc acc gtc acc     384
Pro Tyr Glu Gly Ile Ala Val Phe Asp Gly Lys Lys Ile Thr Val Thr
        115                 120                 125 ggc acc ctg tgg aac ggc aac aag atc tat gac gag aga ctg atc aac     432
Gly Thr Leu Trp Asn Gly Asn Lys Ile Tyr Asp Glu Arg Leu Ile Asn
    130                 135                 140 ccc gac ggc agc ctg ctg ttc aga gtc acc atc aac ggc gtc acc ggc     480
Pro Asp Gly Ser Leu Leu Phe Arg Val Thr Ile Asn Gly Val Thr Gly
145                 150                 155                 160 tgg aga ctg tgc gag aga atc ctg gcc taa                             510
Trp Arg Leu Cys Glu Arg Ile Leu Ala
                165
```

<210> SEQ ID NO 14
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Phe Thr Leu Ala Asp Phe Val Gly Asp Trp Gln Gln Thr Ala Gly Tyr

```
                1               5                      10                      15
              Asn Gln Asp Gln Val Leu Glu Gln Gly Gly Leu Ser Ser Leu Phe Gln
                              20                      25                      30

Ala Leu Gly Val Ser Val Thr Pro Ile Gln Lys Val Val Leu Ser Gly
                              35                      40                      45

Glu Asn Gly Leu Lys Ala Asp Ile His Val Ile Ile Pro Tyr Glu Gly
                              50                      55                      60

Leu Ser Gly Phe Gln Met Gly Leu Ile Glu Met Ile Phe Lys Val Val
              65                      70                      75                      80

Tyr Pro Val Asp Asp His His Phe Lys Val Ile Leu His Tyr Gly Thr
                              85                      90                      95

Leu Val Ile Asp Gly Val Thr Pro Asn Met Ile Asp Tyr Phe Gly Arg
                              100                     105                     110

Pro Tyr Glu Gly Ile Ala Val Phe Asp Gly Lys Lys Ile Thr Val Thr
                              115                     120                     125

Gly Thr Leu Trp Asn Gly Asn Lys Ile Tyr Asp Glu Arg Leu Ile Asn
                              130                     135                     140

Pro Asp Gly Ser Leu Leu Phe Arg Val Thr Ile Asn Gly Val Thr Gly
              145                     150                     155                     160

Trp Arg Leu Cys Glu Arg Ile Leu Ala
                              165

<210> SEQ ID NO 15
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(507)

<400> SEQUENCE: 15 ttt acg ttg gca gat ttc gtt gga gac tgg caa cag aca gct gga tac           48
Phe Thr Leu Ala Asp Phe Val Gly Asp Trp Gln Gln Thr Ala Gly Tyr
1               5                      10                      15 aac caa gat caa gtg tta gaa caa gga gga ttg tct agt ctg ttc caa           96
Asn Gln Asp Gln Val Leu Glu Gln Gly Gly Leu Ser Ser Leu Phe Gln
                20                      25                      30 gcc ctg gga gtg tca gtc acg ccc ata cag aaa gtt gta ctg tct ggg          144
Ala Leu Gly Val Ser Val Thr Pro Ile Gln Lys Val Val Leu Ser Gly
                35                      40                      45 gag aat ggg tta aaa gct gat att cat gtc ata ata cct tac gag gga          192
Glu Asn Gly Leu Lys Ala Asp Ile His Val Ile Ile Pro Tyr Glu Gly
                50                      55                      60 ctc agt ggt ttt caa atg ggt cta att gaa atg atc ttc aaa gtt gtt          240
Leu Ser Gly Phe Gln Met Gly Leu Ile Glu Met Ile Phe Lys Val Val
65                      70                      75                      80 tac ccc gtc gac gac cac cac ttc aag gtc atc ctg cac tac ggc acc          288
Tyr Pro Val Asp Asp His His Phe Lys Val Ile Leu His Tyr Gly Thr
                85                      90                      95 ctg gtc atc gac ggc gtc acc ccc aac atg atc gac tac ttc ggt aga          336
Leu Val Ile Asp Gly Val Thr Pro Asn Met Ile Asp Tyr Phe Gly Arg
                100                     105                     110 ccc tac gag ggc atc gcc gtc ttc gac ggc aag aag atc acc gtc acc          384
Pro Tyr Glu Gly Ile Ala Val Phe Asp Gly Lys Lys Ile Thr Val Thr
                115                     120                     125 ggc acc ctg tgg aac ggc aac aag atc atc gac gag aga ctg atc aac          432
```

```
Gly Thr Leu Trp Asn Gly Asn Lys Ile Ile Asp Glu Arg Leu Ile Asn
            130                 135                 140 ccc gac ggc agc ctg ctg ttc aga gtc acc atc aac ggc gtc acc ggc     480
Pro Asp Gly Ser Leu Leu Phe Arg Val Thr Ile Asn Gly Val Thr Gly
145                 150                 155                 160 tgg aga ctg tgc gag aac atc ctg gcc taa                             510
Trp Arg Leu Cys Glu Asn Ile Leu Ala
                165
```

<210> SEQ ID NO 16
<211> LENGTH: 169
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
                20                  25                  30

Ala Leu Gly Val Ser Val Thr Pro Ile Gln Lys Val Val Leu Ser Gly
            35                  40                  45

Glu Asn Gly Leu Lys Ala Asp Ile His Val Ile Pro Tyr Glu Gly
        50                  55                  60

Leu Ser Gly Phe Gln Met Gly Leu Ile Glu Met Ile Phe Lys Val Val
65                  70                  75                  80

Tyr Pro Val Asp Asp His His Phe Lys Val Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

<210> SEQ ID NO 17
<211> LENGTH: 510
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(507)

<400> SEQUENCE: 17

```
ttc acc ctg gag gac ttc gtc ggc gac tgg aga cag acc gcc ggc tac     48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag     96
Asn Leu Asp Gln Val Leu Glu Gln Gly Gly Val Ser Ser Leu Phe Gln
                20                  25                  30 aac ctg ggc gtc agc gtc acc ccc atc cag aga atc gtc ctt agc ggc    144
Asn Leu Gly Val Ser Val Thr Pro Ile Gln Arg Ile Val Leu Ser Gly
```

```
gag aac ggc ctg aag atc gac atc cac gtc atc atc ccc tac gag ggc      192
Glu Asn Gly Leu Lys Ile Asp Ile His Val Ile Ile Pro Tyr Glu Gly
            50                  55                  60 ctg agc ggc gac cag atg ggc cag atc gag aag atc ttc aag gtc gtc      240
Leu Ser Gly Asp Gln Met Gly Gln Ile Glu Lys Ile Phe Lys Val Val
 65                  70                  75                  80 tac ccc gtc gac gac cac cac ttc aag gtc atc ctg cac tac ggc acc      288
Tyr Pro Val Asp Asp His His Phe Lys Val Ile Leu His Tyr Gly Thr
                     85                  90                  95 ctg gtc atc gac ggc gtc acc ccc aac atg atc gac tac ttc ggt aga      336
Leu Val Ile Asp Gly Val Thr Pro Asn Met Ile Asp Tyr Phe Gly Arg
                100                 105                 110 ccc tac gag ggc atc gcc gtc ttc gac ggc aag aag atc acc gtc acc      384
Pro Tyr Glu Gly Ile Ala Val Phe Asp Gly Lys Lys Ile Thr Val Thr
            115                 120                 125 ggc acc ctg tgg aac ggc aac aag atc atc gac gag aga ctg atc aac      432
Gly Thr Leu Trp Asn Gly Asn Lys Ile Ile Asp Glu Arg Leu Ile Asn
130                 135                 140 ccc gac ggc agc ctg ctg ttc aga gtc acc atc aac ggc gtc acc ggc      480
Pro Asp Gly Ser Leu Leu Phe Arg Val Thr Ile Asn Gly Val Thr Gly
145                 150                 155                 160 tgg aga ctg tgc gag aga atc ctg gcc taa                              510
Trp Arg Leu Cys Glu Arg Ile Leu Ala
                165
```

<210> SEQ ID NO 18
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Phe Thr Leu Glu Asp Phe Val Gly Asp Trp Arg Gln Thr Ala Gly Tyr
 1               5                  10                  15

Asn Leu Asp Gln Val Leu Glu Gln Gly Gly Val Ser Ser Leu Phe Gln
            20                  25                  30

Asn Leu Gly Val Ser Val Thr Pro Ile Gln Arg Ile Val Leu Ser Gly
        35                  40                  45

Glu Asn Gly Leu Lys Ile Asp Ile His Val Ile Ile Pro Tyr Glu Gly
    50                  55                  60

Leu Ser Gly Asp Gln Met Gly Gln Ile Glu Lys Ile Phe Lys Val Val
 65                  70                  75                  80

Tyr Pro Val Asp Asp His His Phe Lys Val Ile Leu His Tyr Gly Thr
                 85                  90                  95

Leu Val Ile Asp Gly Val Thr Pro Asn Met Ile Asp Tyr Phe Gly Arg
            100                 105                 110

Pro Tyr Glu Gly Ile Ala Val Phe Asp Gly Lys Lys Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165
```

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gcggaattct ttacgttggc agatttcgtt gga        33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gccgtcgacg gggtaaacaa ctttgaagat cat        33

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ggcgaattcg gtgggcttgg cctcggccac        30

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
taatacgact cactataggg        20

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gacggcgatg ccagggtagg gtctacc        27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ggtagaccct accctggcat cgccgtc        27

<210> SEQ ID NO 25

```
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcctctagat taggccagga ttctctcgca cagtct                                  36

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccgtcgacg accaccactt caagattatc ctgcactac                               39

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtgacggtg atctgcttgc cgtcgaa                                            27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttcgacggca agcagatcac cgtcacc                                            27

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tagaaggcac agtccagg                                                      18

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagtctctcg tcatagatct tgttgcc                                            27

<210> SEQ ID NO 31
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggcaacaaga tctatgacga gagactg                                              27

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccgtcgacg accaccactt caaggtcatc ctgcact                                   37

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcctctagat taggccagga tgttctcgca cagtct                                    36

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Leu Gly Thr Thr Met Val
1               5
```

CHIMERIC GENES FOR THE CATALYTIC PROTEIN OF *OPLOPHORUS* LUCIFERASE AND USE THEREOF

This application claims benefit of the priority application, Japanese patent application no. 2014-047379, filed on Mar. 11, 2014, which is incorporated by reference herein in its entirety.

SEQUENCE LISTING

The instant application contains a sequence listing which has been submitted in ASCII format via EFS-Web and is hereby incorporated by reference in its entirety. Said ASCII copy, created on Mar. 30, 2015, is named 206313-0015-00-US-523885_SL.txt and is 42,657 bytes in size.

TECHNICAL FIELD

The present invention relates to chimeric genes for the catalytic protein of *Oplophorus* luciferase, use thereof and so on.

BACKGROUND ART

Bioluminescence is a phenomenon based on a chemical reaction in vivo, which is called a luciferin (a luminescence substrate)-luciferase (an enzyme that catalyzes the luminescence reaction) reaction. Numerous studies of the identification of luciferins or luciferases and the elucidation of the luminescence mechanism in a molecular level have been performed for a long time in the country and overseas. In bioluminescent marine organisms, *Oplophorus gracilirostris* luciferase from the deep-sea shrimp is an extracellularly secreted luciferase (Non-Patent Document 1). *Oplophorus* luciferase is a 106 kDa protein composed of a protein with a molecular weight of 35 kDa and a protein with a molecular weight of 19 kDa. The domain that catalyzes the luminescence is found to be 19 kDa protein. *Oplophorus* luciferase uses coelenterazine as a luminescence substrate and is classified as a coelenterazine-type luciferase (Patent Document 1, Non-Patent Document 2). *Oplophorus* luciferase is different from other coelenterazine-type luciferases in broad substrate specificity and uses coelenterazine analogues as a suitable substrate as well as coelenterazine (Non-Patent Document 2). When the gene for the 19 kDa protein is expressed in *Escherichia coli* (*E. coli*) at ambient and lower temperatures, the protein is expressed mostly as an insoluble protein (Non-Patent Document 3). When the 19 kDa protein is expressed as a fusion protein to ZZ domain from protein A in a low temperature expression system, the fused protein can be expressed as a soluble protein (Non-Patent Document 4). It is also reported that when the 19 kDa protein was expressed in animal culture cells, the expressed protein was hardly secreted outside of cells (Non-Patent Document 2).

Recently, it is reported that the mutated 19 kDa protein having catalytic activity of luminescence was prepared by mutating the 16 amino acids of the 19 kDa protein and showed a higher luminescence activity than native 19 kDa protein, and was secreted into an extracellular medium (Patent Document 2, Non-Patent Documents 4 and 5). It is also reported that coelenterazine derivatives displayed higher activity than native coelenterazine used as a substrate (Non-Patent Documents 4 and 5).

In the luminescence reaction system using coelenterazine as a substrate, the luminescence reaction of luciferase proceeds only by a substrate and molecular oxygen. For this reason, a coelenterazine-type luciferase gene is used widely as a reporter assay in an animal cultured cell system at present. *Renilla* luciferase having 311 amino acids is used for a reporter assay inside of cells. For an extracellular reporter assay, the secreted *Gaussia* luciferase which is a secretory luciferase having 168 amino acids is used. When recombinant *Renilla* luciferase and *Gaussia* luciferase are compared in specific activity using coelenterazine as a luminescence substrate, the specific activity of *Renilla* luciferase is about $\frac{1}{100}$ of *Gaussia* luciferase (Non-Patent Documents 5 and 6). On the other hand, the specific activity of mutated 19 kDa protein having catalytic activity of luminescence is $\frac{1}{10}$ as compared to *Gaussia* luciferase, indicating that the mutated 19 kDa protein is obviously inferior as the gene for a reporter assay as a secreted protein.

In view of the foregoing, it has been desired to develop a reporter gene which is an intracellular and secreted luciferase and has a higher luminescence activity than that of native 19 kDa protein when coelenterazine or even its analogue is used as the substrate.

RELATED ART DOCUMENTS

Patent Documents

[Patent Document 1] Japanese Patent No. 4,613,441
[Patent Document 2] Japanese National Publication (Tokuhyo) No. 2012-525819

Non-Patent Documents

[Non-Patent Document 1] O. Shimomura et al. (1978) Biochemistry 17: 994-998.
[Non-Patent Document 2] S. Inouye et al. (2000) FEBS Lett. 481: 19-25.
[Non-Patent Document 3] S. Inouye & S. Sasaki (2007) Protein Express. Purif. 56: 261-268.
[Non-Patent Document 4] M. P. Hall et al. (2012) ACS Chem Biol. 7: 1848-1857.
[Non-Patent Document 5] S. Inouye et al. (2013) Biochem. Biophys. Res. Commun. 437: 23-28.
[Non-Patent Document 6] S. Inouye et al. (2013) Protein Express. Purif. 83: 150-156.

DISCLOSURE OF THE INVENTION

Problem to be Solved by the Invention

Under the foregoing circumstances, a novel luciferase that is distinct from conventional luciferase has been desired.

Means for Solving the Problem

The present inventors have made extensive investigations to solve the problem above. As a result, the inventors have found that 19 kDa protein mutants having catalytic activity of luminescence in which substituted amino acids are introduced into 5 amino acids (isoleucine at position of 90, proline at position of 115, glutamine at position of 124, tyrosine at position of 138 and asparagine at position of 166) provide a higher luminescence activity than native 19 kDa protein having catalytic activity of luminescence, and when the 19 kDa protein is expressed in animal cultured cells, the expressed protein is hardly secreted outside of cells. The present invention has thus been accomplished.

More specifically, the present invention provides the following luciferase mutants, polynucleotides, recombinant vectors, transformants, a method of producing luciferase mutants, kits, a method for performing a luminescence reaction, and so on.

[1] A luciferase mutant of (a) or (b) below:

(a) a luciferase mutant comprising an amino acid sequence, in which tyrosine at position of 138 is substituted with another amino acid and at least 3 amino acids selected from the group consisting of isoleucine, proline, glutamine and asparagine at the positions of 90, 115, 124 and 166 are substituted with other amino acids, in the amino acid sequence of SEQ ID NO: 2; or, (b) a luciferase mutant comprising an amino acid sequence in which tyrosine at position of 138 is substituted with another amino acid and at least 3 amino acids selected from the group consisting of isoleucine at position of 90, proline at position of 115, glutamine at position of 124 and asparagine at position of 166 are substituted with other amino acids, and one or more amino acid(s) is/are substituted with other amino acid(s) at position(s) other than at positions of 4, 11, 18, 27, 33, 43, 44, 54, 68, 72, 75, 90, 115, 124, 138 and 166, in the amino acid sequence of SEQ ID NO: 2, and having a luciferase activity.

[2] The luciferase mutant according to [1] above, wherein the luciferase mutant defined in (b) above is a mutant defined in (c) below:

(c) a luciferase mutant comprising an amino acid sequence in which tyrosine at position of 138 is substituted with another amino acid, at least 3 amino acids selected from the group consisting of isoleucine at position of 90, proline at position of 115, glutamine at position of 124 and asparagine at position of 166 are substituted with other amino acids and 1 to 16 amino acid(s) is/are substituted with other amino acid(s) at position(s) other than at positions of 4, 11, 18, 27, 33, 43, 44, 54, 68, 72, 75, 90, 115, 124, 138 and 166, in the amino acid sequence of SEQ ID NO: 2, and having a luciferase activity.

[3] The luciferase mutant according to [1] or [2] above, wherein said another amino acid substituted for the tyrosine at position of 138 is isoleucine or valine.

[4] The luciferase mutant according to [1] above, wherein the luciferase mutant defined in (a) or (b) above is a luciferase mutant defined in (d) or (e) below:

(d) a luciferase mutant comprising an amino acid sequence of SEQ ID NO: 6, SEQ ID NO: 8, SEQ ID NO: 10, SEQ ID NO: 12 or SEQ ID NO: 16;

(e) a luciferase mutant comprising an amino acid sequence in which one or more amino acid(s) is/are substituted with other amino acid(s) at position(s) other than at positions of 4, 11, 18, 27, 33, 43, 44, 54, 68, 72, 75, 90, 115, 124, 138 and 166, in the amino acid sequence of SEQ ID NO: 6, SEQ ID NO: 8, SEQ ID NO: 10, SEQ ID NO: 12 or SEQ ID NO: 16, and having a luciferase activity.

[5] The luciferase mutant according to [4] above, wherein the luciferase mutant defined in (e) above is a luciferase mutant defined in (f) below:

(f) a luciferase mutant comprising an amino acid sequence in which 1 to 16 amino acid(s) is/are substituted with other amino acid(s) at position(s) other than at positions of 4, 11, 18, 27, 33, 43, 44, 54, 68, 72, 75, 90, 115, 124, 138 and 166, in the amino acid sequence of SEQ ID NO: 6, SEQ ID NO: 8, SEQ ID NO: 10, SEQ ID NO: 12 or SEQ ID NO: 16, and having a luciferase activity.

[6] A polynucleotide comprising a polynucleotide encoding the luciferase mutant according to any one of [1] to [5] above.

[7] A recombinant vector comprising the polynucleotide according to [6] above.

[8] A transformant transformed with the recombinant vector according to [7] above.

[9] A method for producing the luciferase mutant according to any one of [1] to [5] above, which comprises the steps of culturing the transformant of [8] above and producing the luciferase mutant according to any one of [1] to [5] above.

[10] A kit comprising at least one selected from the luciferase mutant according to any one of [1] to [5] above, the polynucleotide according to [6] above, the recombinant vector according to [7] above and the transformant according to [8] above.

[11] The kit according to [10] above, further comprising a luciferin.

[12] The kit according to [11] above, wherein the luciferin is a coelenterazine analogue.

[13] The kit according to [12] above, wherein the coelenterazine analogue is coelenterazine or h-coelenterazine.

[14] A method for performing a luminescence reaction, which comprises contacting the luciferase mutant according to any one of [1] to [5] above with a luciferin.

[15] The method according to [14] above, wherein the luciferin is a coelenterazine analogue.

[16] The method according to [15] above, wherein the coelenterazine analogue is coelenterazine or h-coelenterazine.

[17] A method for assaying the activity of a sequence associated with promoter regulation, which comprises using the polynucleotide according to [6] above as a reporter gene and contacting a luciferase mutant encoded by the reporter gene with a luciferin.

[18] The method according to [17] above, wherein the luciferin is a coelenterazine analogue.

[19] The method according to [18] above, wherein the coelenterazine analogue is coelenterazine or h-coelenterazine.

Effects of the Invention

The present invention provides luciferase mutants that are distinct from the known mutants. In a preferred embodiment of the invention, the luciferase mutants have at least one characteristics selected from a higher activity than that of native 19 kDa protein and/or the reported 19 kDa protein mutants having catalytic activity of luminescence when coelenterazines analogues are used as the luminescence substrate, little secretion outside of cells when expressed in animal cultured cells, and so on.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows the results of SDS-PAGE analysis of the crude enzyme solution (crude extract) of *Escherichia coli* in which WNanoKAZ mutant was expressed using a pCold-ZZ-P vector.

MODE FOR CARRYING OUT THE INVENTION

The present invention will be described below in detail.
1. Luciferase Mutant of the Invention The term luciferase mutant of the present invention refers to a mutant of the protein with a molecular weight of 19 kDa of *Oplophorus* luciferase. Specifically, the luciferase mutant of the present invention is intended to mean a luciferase mutant having substantially the same activity as the luciferase mutant comprising an amino acid sequence in which tyrosine at position of 138 is substituted with another amino acid and at least 3 amino acids selected from the group consisting of isoleucine at position of 90, proline at position of 115, glutamine at position of 124 and asparagine at position of 166 are substituted with other amino acids, in the amino acid sequence of SEQ ID NO: 2.

The term "substantially the same activity" is intended to mean at least one activity selected from luciferase activity, activity for little extracellular secretion when expressed in animal cells, and so on.

The term "luciferase activity" is intended to mean the activity for catalyzing the luminescence reaction using a luciferin (e.g., a coelenterazine analogue) which is used as a substrate, namely, the reaction in which luciferin (e.g., a coelenterazine analogue) is oxidized with molecular oxygen to produce oxyluciferin in its excited state. The excited state of oxyluciferin produced emits visible light and converts to the ground state of oxyluciferin.

Luminescence activity can be determined by the method described in, e.g., Inouye, S. & Shimomura, O. (1977) Biochem. Biophys. Res. Commun. 233, 349-353. Specifically, the luciferase mutant of the present invention is mixed with a luciferin to start the luminescence reaction, and the activity of catalyzing luminescence reaction can be determined using a luminometer. Commercially available luminometers, e.g., Luminescencer-PSN AB2200 (manufactured by Atto Inc.) or Centro 960 luminometer (manufactured by Berthold Inc.) may be used as luminometers.

The luciferin used in the present invention may be any luciferin as far as it is used as a substrate for the luciferase mutants of the present invention. Specifically, the luciferin used in the present invention includes a coelenterazine analogue containing the imidazopyrazinone ring as the backbone.

The coelenterazine analogue is used to mean coelenterazine or its analogues. Coelenterazine analogues include, for example, bis-coelenterazine, deoxyfuran-coelenterazine (furimazine), h-coelenterazine, hcp-coelenterazine, cp-coelenterazine, f-coelenterazine, fcp-coelenterazine, n-coelenterazine, MeO-coelenterazine, e-coelenterazine, cl-coelenterazine, ch-coelenterazine, 3iso-coelenterazine, 3meo-coelenterazine, cf3-coelenterazine, i-coelenterazine, et-coelenterazine, me-coelenterazine, 3me-coelenterazine, ameh-coelenterazine 8-(1-naphthyl)-coelenterazine, 8-(2-naphthyl)-coelenterazine, 8-(2-thienyl)-coelenterazine, 6,8-di(2-thienyl)-coelenterazine, 8-(4-hydroxyphenyl)-coelenterazine, 8-(2-benzothienyl)-coelenterazine, 8-(b-styryl)-coelenterazine, 8-phenyl-coelenterazine, 6-deoxy-coelenterazine, 8-(3-thienyl)-coelenterazine and 8-(3-benzo[b]thienyl)-coelenterazine. Of these coelenterazines analogues, coelenterazine is particularly preferred in the present invention.

These coelenterazine analogues could be synthesized by publicly known methods or may also be commercially available.

The coelenterazine analogues could be synthesized by the methods described in, e.g., Shimomura et al. (1988) Biochem. J. 251, 405-410, Shimomura et al. (1989) Biochem. J. 261, 913-920, Shimomura et al. (1990) Biochem. J. 270, 309-312, Tetrahedron Lett. 38: 6405-6406, WO 2010/090319, Inouye et al. (2010) Anal. Biochem. 407, 247-252 or Inouye et al. (2013) Biocchem. Biophys. Res. Commun. 437, 23-28, or respective modifications thereof. Furimazine may be produced by the method described in Hall et al. (2012) ACS Chem. Biol. 16; 848-1857.

The coelenterazines analogues which are commercially available include, for example, coelenterazine, cf3-coelenterazine and h-coelenterazine manufactured by JNC Corp.; hcp-coelenterazine, cp-coelenterazine, f-coelenterazine, fcp-coelenterazine and n-coelenterazine manufactured by Biotium Inc.; and bis-coelenterazine manufactured by Prolume Ltd. and coelenterazine, furimazine and h-coelenterazine manufactured by Promega Corp.

The "luminescence activity using a luciferin as a substrate" refers to luminescence activity using preferably coelenterazine analogues as the substrate. Preferably, the "luminescence activity using coelenterazine analogues as a substrate" is the luminescence activity in which coelenterazine is used as the substrate.

The "activity for little extracellular secretion when expressed in animal cells" is intended to mean that when the protein is expressed in animal cells, most of the expressed protein is not exported but is retained within the cell, and hardly secreted outside of the cell. The term "little extracellular secretion" is specifically intended to mean that extracellular secretion of the protein occurs in an amount (by weight) of 5% or less, 4% or less, 3% or less, 2% or less, 1% or less, 0.5% or less, 0.1% or less, 0.05% or less, or 0.01% or less, of the expressed protein. Specific examples of the "animal cells" are those later described.

The "luciferase mutant comprising an amino acid sequence in which tyrosine at position of 138 is substituted with another amino acid and at least 3 amino acids selected from the group consisting of isoleucine at position of 90, proline at position of 115, glutamine at position of 124 and asparagine at position of 166 are substituted with other amino acids, in the amino acid sequence of SEQ ID NO: 2" includes, for example, a luciferase mutant defined in (a) or (b) described below.

(a) A luciferase mutant comprising an amino acid sequence in which tyrosine at position of 138 is substituted with another amino acid and at least 3 amino acids selected from the group consisting of isoleucine at position of 90, proline at position of 115, glutamine at position of 124 and asparagine at position of 166 are substituted with other amino acids, in the amino acid sequence of SEQ ID NO: 2; or, (b) a luciferase mutant comprising an amino acid sequence in which tyrosine at position of 138 is substituted with another amino acid, at least 3 amino acids selected from the group consisting of isoleucine at position of 90, proline at position of 115, glutamine at position of 124 and asparagine at position of 166 are substituted with other amino acids and one or more amino acid(s) is/are substituted with other amino acid(s) at position(s) other than at positions of 4, 11, 18, 27, 33, 43, 44, 54, 68, 72, 75, 90, 115, 124, 138 and 166, in the amino acid sequence of SEQ ID NO: 2, and having a luciferase activity.

In (a) and (b) described above, the term "at least 3 amino acids are substituted with other amino acids" is intended to mean that substitution of amino acid residues occurs at 3 or 4 positions selected from positions 90, 115, 124 and 166 in the amino acid sequence of SEQ ID NO: 3.

Specifically, the term "at least 3" in "at least 3 amino acids are substituted with other amino acids" is intended to mean (1) the positions of 90, 115 and 124, (2) the positions of 90, 115 and 166, (3) the positions of 115, 124 and 166, (4) the positions of 90, 124, 166, and (5) the positions of 90, 115, 124 and 166.

The term other amino acids substituted for isoleucine at position of 90 in the amino acid sequence of SEQ ID NO: 2 includes, for example, valine, alanine, methionine, leucine, cysteine, serine or phenylalanine, preferably, valine, alanine, methionine, leucine or cysteine, and more preferably, valine.

The term other amino acids substituted for proline at position of 115 in the amino acid sequence of SEQ ID NO: 2 includes, for example, aspartic acid, glutamic acid, isoaspartic acid, isoglutamic acid, 2-aminoadipic acid, 2-aminosuberic acid, and preferably, glutamic acid.

The term other amino acids substituted for glutamine at position of 124 in the amino acid sequence of SEQ ID NO: 2 includes, for example, lysine, arginine, ornithine, 2,4-diaminobutanoic acid, 2,3-diaminopropionic acid, and preferably, lysine.

The term other amino acids substituted for tyrosine at position of 138 in the amino acid sequence of SEQ ID NO: 2 includes, for example, isoleucine, valine, leucine, methionine, cysteine, is, arginine, lysine, histidine or glutamine, preferably, isoleucine, valine, leucine, methionine, arginine or lysine, and more preferably, isoleucine or valine.

The term other amino acids substituted for aspartic acid at position of 166 in the amino acid sequence of SEQ ID NO: 2 includes, for example, lysine, arginine, ornithine, 2,4-diaminobutanoic acid and 2,3-diaminopropionic acid, and preferably arginine.

Where at least 3 amino acids selected from the group consisting of isoleucine at position of 90, proline at position of 115, glutamine at position of 124 and asparagine at position of 166 are substituted in the amino acid sequence of SEQ ID NO: 2, preferably, isoleucine at position of 90 is valine, proline at position of 115 is glutamic acid, glutamine at position of 124 is lysine and asparagine at position of 166 is arginine.

In (b) above, the term "one or more amino acid(s) is/are substituted with other amino acid(s)" is intended to mean that the substitution of one or a plurality of amino acid residues occur at an optional position(s) in the same sequence and at one or a plurality of positions in the amino acid sequence.

The range of "one or more" in the "one or more amino acids are substituted with other amino acids" is, for example, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2 or 1. In general, the less the number of amino acids substituted, the more preferred. Such proteins may be produced by site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", "Proc. Natl. Acad. Sci. USA, 82, 488 (1985)", etc.

The position(s) of the amino acids which are substituted at the positions other than at positions of 4, 11, 18, 27, 33, 43, 44, 54, 68, 72, 75, 90, 115, 124, 138 and 166 in the amino acid sequence of SEQ ID NO: 2 are not particularly limited, and include position(s) 1 to 20, preferably, 1 to 16, more preferably, 1 to 14, much more preferably, 1 to 12, and most preferably, 1 to 9 (1 to several), selected from the group consisting of positions 1, 2, 3, 13, 14, 15, 25, 30, 36, 70, 83, 106, 128, 153, 156, 157, 159, 162, 163 and 169. In particular, the substitution positions can be position(s) 1 to 9 (1 to several), preferably, 1 to 8, more preferably, 1 to 7, much more preferably, 1 to 6, and most preferably, 1 to 5 (5 or less), selected from the group consisting of positions 1, 2, 3, 13, 14, 153, 159, 163 and 169.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and,

Group G: phenylalanine and tyrosine.

In a preferred embodiment of the invention, the luciferase mutant is a luciferase mutant comprising the amino acid sequence of SEQ ID NO: 6, SEQ ID NO: 8, SEQ ID NO: 10, SEQ ID NO: 12 or SEQ ID NO: 16, more preferably, a luciferase mutant comprising the amino acid sequence of SEQ ID NO: 6, SEQ ID NO: 8, SEQ ID NO: 10 or SEQ ID NO: 16, and most preferably, a luciferase mutant comprising the amino acid sequence of SEQ ID NO: 6.

The luciferase mutant of the present invention may further contain an additional peptide sequence at the N terminus and/or C terminus, preferably at the N terminus. The additional peptide sequence is at least one peptide sequence selected from the group consisting of a peptide sequence for purification, a peptide sequence for expressing the luciferase mutant of the present invention as a soluble protein and an epitope sequence capable of recognizing an antibody. The additional peptide sequence is preferably a peptide sequence for purification. In another preferred embodiment of the invention, the additional peptide sequence is at least one sequence selected from the group consisting of a peptide sequence for purification and a peptide sequence for expressing the luciferase mutant of the present invention as a soluble protein.

Peptide sequences employed in the art may be used as the peptide sequence for purification. The peptide sequence for purification includes, for example, a histidine tag sequence with a consecutive amino acid sequence of at least 4 histidine residues and preferably at least 6 residues, an amino acid sequence with a binding domain of glutathione S-transferase into glutathione, the amino acid sequence of Protein A, etc.

The peptide used to express the luciferase mutant of the present invention as a soluble protein includes, for example, polypeptides represented by formula $(Z)_n$. The amino acid sequences for the polypeptides represented by formula $(Z)_n$ and the nucleic acid sequences encoding the same are described in, e.g., JPA KOKAI No. 2008-99669.

Peptide sequences used in the art can be used as the epitope sequence capable of recognizing an antibody.

The method for acquiring the luciferase mutant of the invention is not particularly limited. The luciferase mutant of the invention may be a protein synthesized by chemical synthesis, or a recombinant protein produced by a genetic engineering technique. When the luciferase mutant of the invention is to be chemically synthesized, synthesis may be carried out by, for example, the Fmoc (fluorenylmethyloxycarbonyl) method or the tBoc (t-butyloxycarbonyl) method. In addition, peptide synthesizers available from Advanced ChemTech, PerkinElmer, Pharmacia, Protein Technology Instrument, Synthecell-Vega, PerSeptive, Shimadzu Corporation, etc. may also be used for chemical synthesis. When the luciferase mutant of the invention is to be produced by a genetic engineering technique, the mutant may be produced by a conventional genetic recombination technique. More specifically, the luciferase mutant of the invention may be produced by inserting a polynucleotide (e.g., DNA) encoding the luciferase mutant of the invention into a suitable expression system. The polynucleotide encoding the luciferase mutant of the invention, expression of the luciferase mutant of the invention in an expression system or the like will be later described.

2. Polynucleotide of the Invention

The present invention also provides a polynucleotide comprising a polynucleotide encoding the luciferase mutant of the invention described above. The polynucleotide of the invention may be any polynucleotide so long as it has a nucleotide sequence encoding the luciferase mutant of the invention, although a DNA is preferred. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a Reverse Transcription Polymerase Chain Reaction (hereinafter abbreviated as RT-PCR) using the total RNA or mRNA fraction prepared from the cell or tissue described above.

The polynucleotide of the invention includes the following polynucleotides.

(i) A polynucleotide comprising a polynucleotide encoding the luciferase mutant comprising an amino acid sequence in which tyrosine at position of 138 is substituted with another amino acid and at least 3 amino acids selected from the group consisting of isoleucine at position of 90, proline at position of 115, glutamine at position of 124 and asparagine at position of 166 are further substituted with other amino acids, in the amino acid sequence of SEQ ID NO: 2; or, (ii) A polynucleotide comprising a polynucleotide encoding the luciferase mutant comprising an amino acid sequence in which tyrosine at position of 138 is substituted with another amino acid, at least 3 amino acids selected from the group consisting of isoleucine at position of 90, proline at position of 115, glutamine at position of 124 and asparagine at position of 166 are further substituted with other amino acids and one or more amino acid(s) is/are substituted with other amino acid(s) at position(s) other than at positions of 4, 11, 18, 27, 33, 43, 68, 72 and 75, in the amino acid sequence of SEQ ID NO: 2, and having a luciferase activity.

The luciferase mutants of (i) and (ii) above are as those described above.

A polynucleotide encoding a protein having a given amino acid sequence, in which one or more amino acids are substituted in the amino acid sequence, can be obtained by using a site-specific mutagenesis technique (see, e.g., Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985), Kunkel, Methods Enzymol. 85, 2763-2766 (1988); etc.), the methods using amber mutation (see, e.g., the gapped duplex method, Nucleic Acids Res., 12, 9441-9456 (1984), etc.), etc.

Alternatively, mutations may also be introduced into the polynucleotide by PCR (cf., e.g., Ho S. N. et al., Gene, 77, 51 (1989), etc.) using a pair of primers bearing on the respective 5' ends a sequence in which the targeted mutation (deletion, addition, substitution and/or insertion) has been introduced.

Also, a polynucleotide encoding a partial fragment of protein, which is one type of the deletion mutant, can be obtained using as the primers an oligonucleotide having a sequence which matches the nucleotide sequence at the 5' end of the region encoding the partial fragment to be produced in the polynucleotide encoding the target protein and an oligonucleotide having a sequence complementary to the nucleotide sequence at the 3' end thereof, and performing PCR in which the polynucleotide encoding the target protein is used as a template.

The polynucleotide of the present invention includes preferably a polynucleotide comprising a polynucleotide encoding the luciferase mutant comprising the amino acid sequence of SEQ ID NO: 6, SEQ ID NO: 8, SEQ ID NO: 10, SEQ ID NO: 12 or SEQ ID NO: 16, and more preferably, a polynucleotide comprising a polynucleotide encoding the luciferase mutant comprising the amino acid sequence of SEQ ID NO: 6.

The polynucleotide encoding the luciferase mutant comprising the amino acid sequence of SEQ ID NO: 6 includes a polynucleotide comprising the nucleotide sequence of SEQ ID NO: 5. The polynucleotide encoding the luciferase mutant comprising the amino acid sequence of SEQ ID NO: 8 includes a polynucleotide comprising the nucleotide sequence of SEQ ID NO: 7. The polynucleotide encoding the luciferase mutant comprising the amino acid sequence of SEQ ID NO: 10 includes a polynucleotide comprising the nucleotide sequence of SEQ ID NO: 9. The polynucleotide encoding the luciferase mutant comprising the amino acid sequence of SEQ ID NO: 12 includes a polynucleotide comprising the nucleotide sequence of SEQ ID NO: 11. The polynucleotide encoding the luciferase mutant comprising the amino acid sequence of SEQ ID NO: 14 includes a polynucleotide comprising the nucleotide sequence of SEQ ID NO: 13. The polynucleotide encoding the luciferase mutant comprising the amino acid sequence of SEQ ID NO: 16 includes a polynucleotide comprising the nucleotide sequence of SEQ ID NO: 15.

In some embodiments of the present invention, the polynucleotide is preferably a polynucleotide comprising a polynucleotide consisting of the nucleotide sequence of SEQ ID NO: 5, SEQ ID NO: 7, SEQ ID NO: 9, SEQ ID NO: 11 or SEQ ID NO: 15, and more preferably, a polynucleotide comprising a polynucleotide consisting of the nucleotide sequence of SEQ ID NO: 5.

The polynucleotide of the present invention may further contain a polynucleotide encoding an additional peptide sequence at the 5' end and/or 3' end, preferably at the 5' end. The polynucleotide encoding the additional peptide sequence includes a polynucleotide encoding at least one peptide sequence selected from the group consisting of a peptide sequence for purification, a peptide sequence for expressing the luciferase mutant of the present invention as a soluble protein, an epitope sequence capable of recognizing an antibody, and the like.

Polynucleotides comprising nucleotide sequences encoding the peptide sequence for purification employed in the art can be used as the polynucleotide encoding the peptide sequence for purification. Examples of the peptide sequence for purification include those as described above.

The polynucleotide encoding the peptide sequence used to express the luciferase mutant of the present invention as a soluble protein includes, for example, polypeptides represented by formula $(Z)_n$. The amino acid sequences for the polypeptides represented by formula $(Z)_n$ and the nucleic acid sequences encoding the same are those as described above.

Polynucleotides comprising nucleotide sequences encoding the epitope sequence capable of recognizing antibodies which are used in the art can be used as the polynucleotide encoding the antibody-recognizing epitope sequence.

3. Recombinant Vector and Transformant of the Invention

The present invention further provides recombinant vectors and transformants comprising the polynucleotides of the present invention described above.

Preparation of Recombinant Vector

The recombinant vector of the invention can be obtained by ligating (inserting) the polynucleotide (DNA) of the invention to (into) an appropriate vector. More specifically, the recombinant vector can be obtained by digesting the purified polynucleotide (DNA) with a suitable restriction enzyme, then inserting into a suitable vector at the restriction enzyme site or multiple-cloning site, and ligating to the vector. The vector for inserting the polynucleotide of the invention is not particularly limited as long as it is replicable in a host, and includes plasmids, bacteriophages, animal viruses, etc. Examples of plasmids include plasmids from *E. coli* (e.g., pBR322, pBR325, pUC118, pUC119, etc.), plasmids from *Bacillus subtilis* (e.g., pUB110, pTP5, etc.) and plasmids from yeast (e.g., YEp13, YEp24, YCp50, etc.). Examples of bacteriophages include, e.g., λ phage. Examples of animal viruses include retroviruses, vaccinia viruses and insect viruses (e.g., baculoviruses). In addition, a pCold I vector, a pCold II vector, a pCold III vector and a pCold IV vector (all manufactured by Takara Bio Inc.), a pcDNA3 vector, a PICZa vector (manufactured by Invitrogen Inc.) and the like may also be suitably used.

The polynucleotide of the present invention is generally ligated in an expressible manner downstream of a promoter in a suitable vector. When the host used for transformation is an animal cell, the promoter is preferably an SV40-derived promoter, retrovirus promoter, metallothionein promoter, heat shock promoter, cytomegalovirus promoter, SRα promoter, CMV promoter, and so on. When the host is a bacterium of the genus *Escherichia*, Trp promoter, T7 promoter, lac promoter, recA promoter, λPL promoter, lpp promoter, etc. are preferred. When the host is a bacterium of the genus *Bacillus*, SPO1 promoter, SPO2 promoter, penP promoter, etc. are preferred. When the host is yeast, PHO5 promoter, PGK promoter, GAP promoter, ADH 1 promoter, GAL promoter, etc. are preferred. When the host is an insect cell, polyhedrin promoter, P10 promoter, etc. are preferred.

A low-temperature expression-inducible promoter may also be suitably used. Examples of the low-temperature expression-inducible promoter include promoter sequences for cold shock genes. The cold shock gene includes, for example, *E. coli* cold shock genes (e.g., cspA, cspB, cspG, cspI and csdA), *Bacillus caldolyticus* cold shock genes (e.g., Bc-Csp), *Salmonella enterica* cold shock genes (e.g., cspE) and *Erwinia carotovora* cold shock genes (e.g., cspG). Among others, cspA promoter, cspB promoter, cspG promoter, cspI promoter, csdA promoter and the like can be advantageously used as the low-temperature expression-inducible promoter.

In addition to the foregoing, the recombinant vector of the invention may further contain, if desired, an enhancer, a splicing signal, a polyA addition signal, a ribosome binding sequence (SD sequence), a selection marker, etc., and provided for use. The selection marker includes, for example, a dihydrofolate reductase gene, an ampicillin resistance gene, a neomycin resistance gene, etc.

Preparation of Transformant

The thus obtained recombinant vector comprising the polynucleotide of the invention is introduced into an appropriate host to prepare the transformant. The host is not particularly limited as long as it is capable of expressing the polynucleotide (DNA) of the invention, and may be bacteria of the genera *Escherichia, Bacillus, Pseudomonas* and *Rhizobium*, yeast, animal cells, insect cells, etc. Bacteria of the genus *Escherichia* include *Escherichia coli*, etc. Bacteria of the genus *Bacillus* include *Bacillus subtilis*, etc. Bacteria of the genus *Pseudomonas* include *Pseudomonas putida*, etc. Bacteria of the genus *Rhizobium* include *Rhizobium meliloti*, etc. Yeast includes *Saccharomyces cerevisiae, Schizosaccharomyces pombe*, etc. Animal cells include primary cell cultures, iPS cells, cultured cell lines (CHO cells, HEK293 cells, HL-60 cells, HeLa cells, MDCK cells, NIH3T3cells, PC12 cells), etc. Insect cells include Sf9, Sf21, etc.

The method of transfecting the recombinant vector into the host and the method of transformation by the same can be performed according to various general methods. The method for transfecting the recombinant vector into the host cell includes the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes the method described in Molecular & General Genetics, 168, 111 (1979), etc. The method for transforming yeast includes the method described in Proc. Natl. Acad. Sci. USA, 75, 1929 (1978), etc. The method for transformation of animal cells includes the method described in Virology, 52, 456 (1973), etc. The method for transformation of insect cells includes the method described in Bio/Technology, 6, 47-55 (1988), etc. Thus, the transformant transformed with the recombinant vector comprising the polynucleotide encoding the luciferase mutant of the invention (the polynucleotide of the invention) can be obtained.

Expression Vector and Transformant Comprising Low-Temperature Expression-Inducible Promoter Sequence An expression vector comprising the low-temperature expression-inducible promoter sequence is preferred as the expression vector among others.

Specifically, the expression vector comprising the low-temperature expression-inducible promoter sequence is intended to mean an expression vector comprising the following promoter sequence and coding sequence:

(1) a low-temperature expression-inducible promoter sequence; and, (2) a coding sequence comprising the polynucleotide of the invention.

The low-temperature expression-inducible promoter sequence is intended to mean a promoter sequence which is capable of inducing expression of the protein by lowering the temperature from the culture conditions under which host cells can grow. Examples of the low-temperature expression-inducible promoter are promoters for genes encoding cold shock proteins (cold shock genes). Examples of the cold shock gene promoters include those as described above.

The temperature at which the low-temperature expression-inducible promoter used in the invention is capable of inducing expression is generally 30° C. or less, preferably 25° C. or less, more preferably 20° C. or less, and most preferably 15° C. or less. In order to induce the expression more efficiently, however, the expression induction is generally performed at 5° C. or more, preferably at 10° C. or more, and most preferably at approximately 15° C.

In preparing the expression vector of the invention comprising the low-temperature expression-inducible promoter sequence, the pCold I vector, pCold II vector, pCold III vector and pCold IV vector (all manufactured by Takara Bio Inc.) can be suitably used as the vector for insertion of the polynucleotide of the invention. The protein can be produced as a soluble protein in the cytoplasm in a host cell when expression is performed in a prokaryotic host cell using these vectors.

Prokaryotic cells are preferred as the host into which the expression vector comprising the low-temperature expression-inducible promoter sequence is introduced, more preferably, E. coli, and particularly preferably, the BL21 and JM109 strains. Among others, the BL21 strain is most preferred.

Temperatures for incubation at which the transformant carrying the expression vector comprising the low-temperature expression-inducible promoter sequence grows are generally 25 to 40° C. and preferably 30 to 37° C. Temperatures for inducing the expression are generally 4 to 25° C., preferably 10 to 20° C., more preferably 12 to 18° C., and most preferably 15° C.

4. Production of Luciferase Mutant of the Invention

The present invention further provides a method for producing the luciferase mutant of the invention, which comprises the steps of culturing the transformant described above to produce the luciferase mutant of the invention. The luciferase mutant of the invention can be produced, for example, by culturing the transformant described above under conditions where the polynucleotide (DNA) encoding the luciferase mutant of the invention can be expressed, producing/accumulating and then separating/purifying the luciferase mutant of the invention.

Incubation of Transformant

The transformant of the invention can be incubated in a conventional manner used for incubation of a host. By the incubation, the luciferase mutant of the invention is produced by the transformant and accumulated within the transformant or in the culture medium.

The medium used for culturing the transformant using bacteria of the genus Escherichia or the genus Bacillus as a host may be any of a natural medium and a synthetic medium as far as it is a medium which contains carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed with the expression vector using an inducible promoter is cultured, an inducer may also be added to the medium, if necessary. For example, when the transformant transformed with an expression vector using a Lac promoter is cultured, isopropyl-β-D-thiogalactopyranoside (IPTG), etc. may be added to the medium and indoleacrylic acid (IAA), etc. may be added to the medium in culturing the transformant transformed with an expression vector using a trp promoter.

When the host is bacteria of the genus Escherichia, incubation is performed generally at approximately 15 to 43° C. for approximately 3 to 24 hours. If necessary, aeration and agitation may be applied. When the host is bacteria of the genus Bacillus, incubation is performed generally at approximately 30 to 40° C. for approximately 6 to 24 hours. If necessary, aeration and agitation may be applied.

Medium for incubation of the transformant when the host is yeast include Burkholder's minimal medium (Proc. Natl. Acad. Sci. USA, 77, 4505 (1980)) and an SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20 to 35° C. for approximately 24 to 72 hours. If necessary, aeration and agitation may be applied.

Medium for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30 to 40° C. for approximately 15 to 60 hours. If necessary, aeration and agitation may be applied.

Medium for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 days. If necessary, aeration and agitation may be applied.

Temperatures for incubation at which the transformant transformed with the expression vector comprising the low-temperature expression-inducible promoter sequence and temperatures for expression induction are as described above.

Separation/Purification of Luciferase Mutant of the Invention

The luciferase mutant of the invention can be obtained by separating/purifying the luciferase mutant of the invention from the culture described above. As used herein, the culture is intended to mean any one of a culture broth, cultured cells or cultured bacteria and a cell lysate of the cultured cells or cultured bacteria. The luciferase mutant of the invention can be separated and purified in a conventional manner.

Specifically, when the luciferase mutant of the invention accumulates in the cultured bacteria or cultured cells, after completion of the incubation the bacteria or cells are disrupted in a conventional manner (e.g., ultrasonication, lysozyme, freezing and thawing, etc.,) and then a crude extract of the luciferase mutant of the invention can be obtained in a conventional manner (e.g., centrifugation, filtration, etc.). When the luciferase mutant of the invention accumulates in the periplasmic space, after completion of the incubation the extract containing the luciferase mutant of the invention can be obtained in a conventional manner (e.g., the osmotic shock method, etc.). When the luciferase mutant of the invention accumulates in the culture broth, after completion of the incubation the culture supernatant containing the luciferase mutant of the invention can be obtained by separating the bacteria or cells and the culture supernatant in a conventional manner (e.g., centrifugation, filtration, etc.).

The luciferase mutant of the invention contained in the extract or culture supernatant thus obtained can be purified by conventional methods of separation and purification. Examples of these methods for separation and purification which may be used include ammonium sulfate precipitation, gel filtration chromatography, ion-exchange chromatography, affinity chromatography, reversed-phase high-performance liquid chromatography, dialysis, ultrafiltration, etc., alone or in a suitable combination thereof. When the luciferase mutant of the invention contains the peptide sequence for purification described above, it is preferred to perform purification using the same. Specifically, when the luciferase mutant of the invention contains a histidine tag sequence, nickel chelate affinity chromatography may be used; when the luciferase mutant of the invention contains the binding domain of S-transferase to glutathione, affinity chromatography with a glutathione-binding gel may be used; when the luciferase mutant of the invention contains the amino acid sequence of Protein A, antibody affinity chromatography may be used.

5. Use of Luciferase Mutant of the Invention

Use as Detection Marker by Luminescence

The luciferase mutant of the invention can be used as a detection marker which emits luminescence in the presence of a luciferin (hereinafter "detection marker of the present invention"). The detection marker of the present invention can be utilized for detection of the target substance in, e.g., an immunoassay, a hybridization assay, etc.

The luciferase mutant of the invention can be expressed, e.g., as a fusion protein with a target protein, and introduced into cells by means of the microinjection method, etc., and the resulting product can be used to determine distribution of the target protein described above. The distribution of such a target protein or the like can be determined by using detection methods such as luminescence imaging. In addition to the introduction into cells by means of the microinjection method or the like, the luciferase mutant of the invention can be expressed in cells to provide for use.

The luminescence substrate (luciferin) used is preferably coelenterazines analogues, and particularly preferably, coelenterazine.

Use as Reporter Protein

The luciferase mutant of the invention may also be used as a reporter protein to assay the transcription activity of promoters, etc. In this case, the polynucleotide of the invention is used as a reporter gene and the luciferase mutant encoded by the reporter gene is contacted with luciferin. As used herein, the term "contact" is intended to mean that the luciferase mutant of the invention and a luciferin are allowed to be present in the same reaction system or culture system, which includes, for example, addition of a luciferin to a culture container charged with cells expressing the luciferase mutant of the invention, mixing the cells with a luciferin, and incubation of the cells in the presence of a luciferin. The polynucleotide encoding the luciferase mutant of the invention (i.e., the polynucleotide of the invention) is fused to a target promoter or some other expression control sequence (e.g., an enhancer, etc.) to construct a vector. By introducing the vector into a host cell and detecting the luminescence from the luciferase mutant of the invention in the presence of a luciferin (luminescence substrate), the activity of the target promoter or some other expression control sequence can be assayed. Furthermore, the expressed luciferase mutant is reacted with coelenterazines analogues and the luminescence generated may also be visualized in pictures by using a high-sensitive detector.

The luciferin used is preferably coelenterazines analogues, and particularly preferably, coelenterazine, as described above.

The cells used are preferably animal cells. In a preferred embodiment of the invention, the luciferase mutant is hardly secreted outside of cells in the case of animal cells.

The polynucleotide of the invention can be used as a reporter gene in such a manner as described above.

Material for Amusement Supplies

The luciferase mutant of the invention has the activity of catalyzing the reaction where a luciferin is oxidized with oxygen molecules to form oxyluciferin in its excited state. The oxyluciferin in the excited state emits visible light to decay to the ground state. Accordingly, the luciferase mutant of the invention can be used preferably as a luminescent material for amusement supplies. Examples of such amusement supplies are luminescent soap bubbles, luminescent ice bars, luminescent candies, luminescent color paints, etc. These amusement supplies of the invention can be prepared in a conventional manner.

The luciferin used is preferably coelenterazines analogues, and particularly preferably, coelenterazine, as described above.

Bioluminescence Resonance Energy Transfer (BRET) Method

By utilizing the principle of interaction between molecules by the bioluminescence resonance energy transfer (BRET) method, the luciferase mutant of the invention is available for analytical methods such as analysis of physiological functions, assay of enzyme activities, etc.

For instance, when the luciferase mutant of the invention is used as a donor and the fluorescent substance (e.g., an organic compound, a fluorescent protein, etc.) is used as an acceptor, the interactions between the donor and acceptor above can be detected by inducing bioluminescence resonance energy transfer (BRET) between them.

In an embodiment of the present invention, the organic compound used as an acceptor includes Hoechist3342, Indo-1, DAP1, etc. In another embodiment of the present invention, the fluorescent protein used as an acceptor includes a green fluorescent protein (GFP), a blue fluorescent protein (BFP), a muted GFP fluorescent protein, phycobilin, etc.

In a preferred embodiment of the present invention, the physiological functions to be analyzed include an orphan receptor (especially, a G protein-coupled receptor), apoptosis, transcription regulation by gene expression, etc. In a further preferred embodiment of the present invention, the enzyme to be analyzed is protease, esterase, kinase, or the like.

Analysis of the physiological functions by the BRET method can be performed by known methods, for example, by modifications of the method described in Biochem. J. 2005, 385, 625-637 or Expert Opin. Ther Tarets, 2007 11: 541-556. Enzyme activities may also be assayed by known methods, for example, by modifications of the method described in Nature Methods 2006, 3:165-174 or Biotechnol. J. 2008, 3:311-324.

The luciferin used is preferably coelenterazines analogues, and particularly preferably, coelenterazine, as described above.

6. Kit of the Invention

The present invention also provides a kit comprising any one selected from the luciferase mutant of the invention, the polynucleotide of the invention, the recombinant vector of the invention and the transformant of the invention. The kit of the invention may further contain a luciferin.

The luciferin used is preferably coelenterazines analogues, and particularly preferably, coelenterazine, as described above.

The kit of the present invention may be prepared with conventional materials by conventional methods. The kit of the present invention may further contain, e.g., sample tubes, plates, instructions for the kit user, solutions, buffers, reagents, and samples suitable for standardization or control samples. The kit of the present invention may further contain salts including halide ions.

The kit of the present invention can be used for the aforesaid measurement using a reporter protein or a reporter gene, the detection marker with luminescence, or the analysis of physiological functions or measurement of enzyme activities by the BRET method. The kit can also be used in the method for luminescence reaction as described below.

7. Method for Luminescence Reaction

Luminescence Activity

The luciferase mutant of the invention has the ability of catalyzing the reaction which involves oxidization of a luciferin with oxygen molecules to form an oxyluciferin in its excited state. The oxyluciferin in the excited state emits light on returning to the ground state. That is, the luciferase mutant of the invention catalyzes the luminescence reaction in which a luciferin is used as a substrate to cause luminescence. This activity is sometimes referred to as "the luminescence activity" in the specification.

Luminescence Reaction

The luminescence reaction using the luciferase mutant of the invention in which a luciferin is used as a substrate can be performed by contacting the luciferase mutant of the invention with the luciferin. As used herein, the term "contact" is intended to mean that the luciferase mutant of the invention and a luciferin are allowed to be present in the same reaction system, which includes, for example, addition of the luciferase mutant of the invention to a container charged with a luciferin, addition of a luciferin to a container charged with the luciferase mutant of the invention and mixing the luciferase mutant of the invention with a luciferin. The reaction can be carried out under conditions conventionally used for the luminescence reaction using *Oplophorus* luciferase or under conditions modified therefrom.

Specifically, solvents for the reaction which are employed are, for example, a buffer solution such as Tris-HCl buffer, sodium phosphate buffer, etc., water, and the like.

Temperatures for the reaction are generally approximately 4° C. to 40° C. and preferably approximately 4° C. to 25° C.

In the reaction solution, pH is generally approximately 5 to 10, preferably approximately 6 to 9, more preferably approximately 7 to 8 and most preferably approximately 7.5.

The luciferin is preferably coelenterazines analogues, and particularly preferably, coelenterazine, as described above.

The luciferin may also be added to the reaction system in the form of a solution in a polar solvent such as dimethylformamide, dimethylsulfoxide, etc., or in an alcohol such as methanol, ethanol, butanol, etc.

Activation of Luminescence Activity

Luciferase activity of the luciferase mutant of the invention can be activated by halide ions, nonionic surfactants, etc.

Examples of the halide ions are fluorine ions, chlorine ions, bromine ions and iodine ions; preferred are chlorine ions, bromine ions and iodine ions.

The concentration of halide ions is generally approximately 10 µM to 100 mM, preferably approximately 100 µM to 50 mM and particularly preferably approximately 1 mM to 20 mM.

Addition of the halide ions to the reaction system is performed by a method which comprises adding the halide ions in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI, KF, KCl, KBr, KI, $CaF_2$, $CaCl_2$, $CaBr_2$, $CaI_2$, $MgF_2$, $MgCl_2$, $MgBr_2$, $MgI_2$, etc.

Examples of nonionic surfactants which are commercially available (trade name) include Tween 20 (polyoxyethylene sorbitan monolaurate), Tween 80 (polyoxyethylene sorbitan monooleate), Triton X-100 (polyethylene glycol-p-isooctyl-phenyl ether), Briji-58 (polyoxyethylene (20) cetyl ether), Nonidet P-40 (ethylphenolpoly(ethylene glycol ether)n), etc., and preferably, Tween 20, Triton X-100, etc.

Concentration of the nonionic surfactant is generally approximately 0.0002% (w/v) to 0.2% (w/v), preferably, approximately 0.001% (w/v) to 0.1% (w/v), and particularly preferably, approximately 0.05% (w/v) to 0.02% (w/v).

Regardless of their purposes, all of the documents and publications described in the specification are incorporated herein by reference, each in its entirety.

Unless otherwise indicated with respect to the embodiments and working examples, the methods described in standard sets of protocols such as J. Sambrook, E. F. Fritsch & T. Maniatis (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., etc. or modifications or variations thereof are used. When commercially available reagent kits or measuring apparatuses are used, protocols attached thereto are used unless otherwise indicated.

The objects, characteristics and advantages of the present invention as well as the idea thereof are apparent to those skilled in the art from the descriptions given herein. Based on the description given herein, those skilled in the art can easily reproduce the present invention.

It can be understood that the embodiments of the invention, specific working examples, etc. are disclosed as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to specific examples but is not deemed to be limited thereto.

Example 1: Preparation of Chimeric Gene of 19kOLase (KAZ) and nanoKAZ

A chimeric gene of the 19 kDa protein (hereinafter also designated as 19kOLase or KAZ) of native *Oplophorus* luciferase having luminescence activity and nanoKAZ (hereinafter designated as WNanoKAZ gene) was prepared by the following procedure. PCR was performed with two PCR primers using a PCR Kit (manufactured by Takara Bio Inc.) in which the vector pCold-ZZ-KAZ for soluble expression of native 19kOLase protein (nucleotide sequence of SEQ ID NO: 1, amino acid sequence of SEQ ID NO: 2) described in Inouye et al. (2008) Biochem. Biophys. Res. Commun. 376: 448-453 was used as a template (cycle conditions: 25 cycles; 1 min/94° C., 1 min/50° C., 1 min/72° C.). Specifically, the DNA fragment carrying the recognition sites for restriction enzyme EcoRI at the 5' end and restriction enzyme SalI at the 3' end of the gene encoding position 1 to 82 of the amino acid sequence of SEQ ID NO: 2 was prepared by PCR.

Primers Used to Prepare the DNA Fragment:

```
KAZ-8N/EcoRI
                                        (SEQ ID NO: 19)
(5'gcg GAA TTC TTT ACG TTG GCA GAT TTC GTT GGA 3')

KAZ-31/SalI247-R
                                        (SEQ ID NO: 20)
(5'gcc GTC GAC GGG GTA AAC AAC TTT GAA GAT CAT 3')
```

The DNA fragment amplified by PCR with the primers above was purified using a PCR purification kit (manufactured by Qiagen, Inc.) and digested with the restriction enzymes of EcoRI/SalI in a conventional manner.

On the other hand, the pCold-ZZ-P-nanoKAZ vector for soluble expression of the mutated KAZ with 16 mutations (SEQ ID NO: 4, hereinafter also designated as nanoKAZ) described in Inouye et al (2013) Biochem. Biophys. Res. Commun. 437: 23-28 was digested with the restriction enzymes of EcoRI and SalI to give the pCold-ZZ-P-vector carrying the gene encoding position 83 to 169 of the amino acid sequence of nanoKAZ of SEQ ID NO: 4, followed by ligation with the gene fragment encoding position 1 to 82 of the amino acid sequence of native KAZ described above. As a result, the expression vector pCold-ZZ-P-WNanoKAZ for the chimeric protein having the amino acid sequence of position 1 to 82 of native KAZ and the amino acid sequence of position 83 to 169 of nanoKAZ was obtained.

The nucleotide sequence of the insert DNA (WNanoKAZ gene) in pCold-ZZ-P-WNanoKAZ is shown in SEQ ID NO: 5. The amino acid sequence of the protein encoded by the WNanoKAZ gene (hereinafter designated as WNanoKAZ) is shown in SEQ ID NO: 6. The amino acid substitutions in the KAZ protein by constructing the chimeric (WNanoKAZ) gene are 5 positions shown in TABLE 1.

TABLE 1

Substituted amino acids and nucleotides in WNanoKAZ

| Substituted position of amino acid | Nucleotide sequence Substitution (before) (Wild type = KAZ) | Substitution (after) (WNanoKAZ) |
|---|---|---|
| I90V | 268 ATT (I) | 268 GTC (V) |
| P115E | 343 CCT (P) | 343 GAG (E) |
| Q124K | 370 CAG (Q) | 370 AAG (K) |

TABLE 1-continued

Substituted amino acids and nucleotides in WNanoKAZ

| Substituted position of amino acid | Nucleotide sequence Substitution (before) (Wild type = KAZ) | Substitution (after) (WNanoKAZ) |
|---|---|---|
| Y138I | 412 TAT (Y) | 412 ATC (I) |
| N166R | 496 AAC (N) | 496 AGA (R) |

Example 2: Expression of WNanoKAZ in *E. coli* and Preparation of Crude Enzyme Solution In order to express WNanoKAZ in *E. coli*, pCold-ZZ-P-WNanoKAZ obtained in EXAMPLE 1 was used. The *E. coli* BL21 strain (Novagen, Madison, Wis.) was used as a host cell. The BL21 strain carrying the recombinant plasmid was incubated in 5 mL of Luria-Bertani medium (hereinafter designated as LB medium) containing ampicillin (50 µg/mL) at 37° C. for 17 hours. The seed culture of 0.1 mL was inoculated to 10 mL of LB medium and incubated for 3 hours, followed by cooling in freezing water for 1 hour. IPTG was added to the culture medium at a final concentration of 0.1 mM, followed by incubation at 15° C. for further 19 hours. After completion of the incubation, 1 mL of the culture medium was collected by centrifugation at 10,000 rpm for 2 minutes. The collected *E. coli* cells were suspended in 0.5 mL of 30 mM Tris-HCl (pH 7.6)-10 mM EDTA. The cells were disrupted by sonication for 3 seconds using a Branson Model 250 Sonifire (Danbury, Conn.) to give a crude enzyme solution. Then, DTT was added to the crude enzyme solution at a final concentration of 1 mM. After the mixture was allowed to stand in freezing water over 8 hours or more, the luminescence activity was measured.

Example 3: Assay for Luminescence Activity of WNanoKAZ in Crude Enzyme Solution 1 µl of the crude enzyme solution obtained in EXAMPLE 2 was added to 100 µl of 30 mM Trix-HCl (pH 7.6)-10 mM EDTA (Wako Pure Chemical Industries, Ltd.) containing 1 µg of coelenterazine (manufactured by JINC Corp.), luminescence reaction was started. Luminescence activity was measured for 60 seconds using a luminometer (manufactured by Atto Inc.: AB2200); the maximum intensity of luminescence ($I_{max}$) was given as a relative luminescence activity.

As a result, WNanoKAZ displayed 64-fold higher activity than native KAZ, and dnKAZ (amino acid sequence of SEQ ID NO: 18; in nanoKAZ the KLGTTMV peptide (SEQ ID NO: 34) is added to the N terminus of dnKAZ), which is the mutated KAZ with 16 mutations, displayed 7.4-fold higher activity than that of native KAZ, as shown in TABLE 2. The luminescence activity was enhanced by introducing amino acid substitutions at 5 positions.

TABLE 2

Luminescence activity of WNanoKAZ, KAZ and dnKAZ in crude enzyme solution

| Expression vector (pCold-ZZ-P-) | Relative luminescence activity ($I_{max}$) |
|---|---|
| KAZ | 1.0 |
| WNanoKAZ | 64 |
| dnKAZ | 7.4 |

Example 4: Secretory Expression Vector for WNanoKAZ Using the Secretory Signal Peptide Sequence of *Gaussia* Luciferase The expression vector for WNanoKAZ was constructed as follows. Firstly, a novel vector pcDNA3-GLsp for expression in animal cultured cells was constructed. Specifically, the secretory signal peptide sequence of *Gaussia* luciferase was obtained from pcDNA3-GLuc vector (manufactured by Prolume Ltd.) by PCR using the GLsp-1R/EcoRI primer (SEQ ID NO: 21: 5' ggc GAA TTC GGT GGG CTT GGC CTC GGC CAC 3', EcoRI sequence underlined) and T7 primer (SEQ ID NO: 22: 5' TAATACG ACTCAC-TATAGGG 3') by PCR. After digesting with HindIII/EcoRI, the resultant fragment was inserted into the HindIII/EcoRI site of pcDNA3 vector (manufactured by Invitrogen Inc.) to construct a novel expression vector pcDNA3-GLsp. That is, the novel expression vector is under the control of the CMV promoter, followed by the Kozak sequence, the secretory signal peptide sequence of *Gaussia* luciferase and a multiple-cloning site sequence.

Next, the expression vector for WNanoKAZ was constructed as follows, using the novel expression vector pcDNA3-GLsp. The DNA fragment obtained in EXAMPLE 1 was digested with the restriction enzymes of EcoRI/XbaI in a conventional manner and then ligated to the EcoRI-XbaI site of pcDNA3-GLsp to construct the expression vector pcDNA3-GLsp-WNanoKAZ. The gene sequence inserted was confirmed by sequencing using a DNA Sequencer (manufactured by ABI Inc.). As a result, it was confirmed that the insert gene sequence was the nucleotide sequence shown by SEQ ID NO: 5 (WNanoKAZ), and the amino acid sequence encoded by the gene sequence was the amino acid sequence shown by SEQ ID NO: 6 (WNanoKAZ).

Example 5: Transfection of Vectors into Animal Culture Cells and Preparation of Enzyme for Assay (1) Purification of Expression Plasmid The following experiment was performed using pcDNA3-GLsp-WNanoKAZ obtained in EXAMPLE 4. The recombinant plasmid was purified from *E. coli* JM83 strain using a plasmid purification kit (manufactured by QIAGEN) and dissolved in sterile water. The firefly luciferase vector (pGL4.13 [Luc2/sv40]: manufactured by Promega Corp.) was similarly prepared and used as an internal standard.

(2) Transfection and Preparation of Enzyme for Assay

Chinese hamster ovary cell line CHO-K1 was cultured in Ham's F-12 medium (manufactured by Wako Pure Chemical Industries, Ltd.) supplemented with 10% (v/v) fetal bovine serum (manufactured by Biowest Inc.). The CHO-K1 cells were seeded in a 6-well plate in 1×10⁵ cells/well/2 mL medium (n=2) and cultured in an incubator at 37° C. in 5% (v/v) $CO_2$. After 24 hours, the purified recombinant plasmid was transfected to CHO-K1 cells using a FuGene HD transfection kit (manufactured by Promega Corp.) and the cells were used for subsequent experiment. Specifically, 1 µg of the recombinant plasmid, 0.1 µg of the internal standard vector pGL4.13 [Luc2/sv40] and 3 µL of FuGene HD were added to 100 µL of the medium and allowed to stand at room temperature for 15 minutes. Subsequently, 100 µL of the DNA-FuGene complex solution was added to the cells in the 6-well plate. After incubation for 46 hours, the culture medium was collected. On the other hand, the KAZ mutant expressed in the cells was washed 3 times with 3 mL of 1×PBS, then suspended in 1 mL of 1×PBS and disrupted by sonication on ice. The resultant cell extract of WNanoKAZ was used as the enzyme solution.

Example 6: Assay for Luminescence Activity of KAZ Mutants Expressed in Animal Cultured Cells After adding 5 µL of the culture medium and cell extract obtained in EXAMPLE 5 to 100 µL of 30 mM Tris-HCl (pH 7.6)-10 mM EDTA (Wako Pure Chemical Industries, Ltd.) containing 1 µg of coelenterazine (manufactured by JNC Corp.), a luminescence reaction was started. Luminescence activity was measured for 60 seconds using a luminometer (manufactured by Atto Inc.: AB2200). The maximum intensity of luminescence ($I_{max}$) was given as a percentage (%). The results reveal that extracellular secretion was not observed, as shown in TABLE 3.

TABLE 3

Luminescence activity of WnanoKAZ, KAZ and dnKAZ expressed in animal culture cells

| Expression vector | Relative luminescence activity (%, $I_{max}$) | |
|---|---|---|
| (pcDNA3-GLsp-) | Culture medium | Cell extracts |
| KAZ | 0.1 | 0.2 |
| WNanoKAZ | <0.01 | 22 |
| dnKAZ | 100 | 16 |

Regarding firefly luciferase used as an internal standard to confirm the efficiency of transfection, 5 µL of the cell extract obtained in EXAMPLE 5 was added to 100 µL of a reagent for enzyme assay (Promega Corp.) to start a luminescence reaction. Luminescence activity was measured for 10 seconds in terms of the maximum intensity of luminescence (flu), using a luminometer (manufactured by Atto Inc.: AB2200). The results reveal that the transfection efficiencies were almost the same.

Example 7: Construction of Single Amino Acid-Substituted Mutant Gene for WNanoKAZ WNanoKAZ displayed 64-fold higher activity than that of dnKAZ as shown in EXAMPLE 3, when coelenterazine was used as the substrate. The higher activity is considered to be due to amino acid substitutions at 5 positions, in contrast to native KAZ. In order to identify amino acid residues associated with the increased activity, a mutant in which the substituted amino acid residues at 5 positions were replaced with the amino acid residues from native KAZ was constructed to examine its effects on luminescence activity.

Amino acid substitution to the WNanoKAZ gene by site-directed mutagenesis was performed by PCR by the procedure described in Ho et al., Gene (1989) 77: 51-59. Specifically, PCR (cycle conditions: 25 cycles of 1 min/94° C., 1 min/50° C. and 1 min/72° C.) was performed with a PCR kit (manufactured by Takara Bio Inc.) using as a temperate pCold-KAZ or pCold-ZZ-KAZ carrying the WNanoKAZ gene and two PCR primers.

To construct, e.g., single amino acid-substituted mutant gene WNanoKAZ-E115P, were prepared DNA fragments amplified by the following primers using as the template pcDNA3-GLsp-WNanoKAZ obtained in EXAMPLE 4.

Primers Used to Prepare DNA Fragments:

KAZ-8N/EcoRI
(SEQ ID NO: 19)
(5' gcg GAA TTC TTT ACG TTG GCA GAT TTC GTT GGA 3')

nanoKAZ: E115P-R
(SEQ ID NO: 23)
(5' GAC GGC GAT GCC AGG GTA GGG TCT ACC 3')

nanoKAZ: E115P-F
(SEQ ID NO: 24)
(5' GGT AGA CCC TAC CCT GGC ATC GCC GTC 3')

nanoKAZ-3C/XbaI
(SEQ ID NO: 25)
(5' gcc TCT AGA TTA GGC CAG GAT TCT CTC GCA CAG TCT 3')

The second PCR was carried out using the DNA fragments obtained above at the two sites and PCR primers of KAZ-8N/EcoRI and nanoKAZ-3C/XbaI (SEQ ID NO: 25). As a result, the WNanoKAZ gene region (WNanoKAZ-E115P) with substitution of proline for glutamic acid at amino acid position 115 in the amino acid sequence of SEQ ID NO: 6 was amplified.

Amino acid-substituted WNanoKAZ gene regions were obtained in a similar manner using the templates and primers listed in TABLE 4.

TABLE 4

Templates and PCR primers used for single amino acid substitution in WNanoKAZ protein

| Substituted position | | Template | | Primer name | Sequence |
|---|---|---|---|---|---|
| V90I | PCR | pcDNA3-GLsp-WNanoKAZ | a | nanoKAZ: V90I-F | 5' gcc GTC GAC GAC CAC CAC TTC AAG ATT ATC CTG CAC TAC 3' (SEQ ID NO: 26) |
| | | | b | nanoKAZ-3C/XbaI | 5' gcc TCT AGA TTA GGC CAG GAT TCT CTC GCA CAG TCT 3' (SEQ ID NO: 25) |
| E115P | 1st PCR | pcDNA3-GLsp-WNanoKAZ | a | KAZ-8N/EcoRI | 5' gcg GAA TTC TTT ACG TTG GCA GAT TTC GTT GGA 3' (SEQ ID NO: 19) |
| | | | b | nanoKAZ: E115P-R | 5' GAC GGC GAT GCC AGG GTA GGG TCT ACC 3' (SEQ ID NO: 23) |
| | | pcDNA3-GLsp-WNanoKAZ | c | nanoKAZ: E115P-F | 5' GGT AGA CCC TAC CCT GGC ATC GCC GTC 3' (SEQ ID NO: 24) |
| | | | d | nanoKAZ-3C/XbaI | 5' gcc TCT AGA TTA GGC CAG GAT TCT CTC GCA CAG TCT 3' (SEQ ID NO:25) |
| | 2nd PCR | 1st PCR product | a | KAZ-8N/EcoRI | 5' gcg GAA TTC TTT ACG TTG GCA GAT TTC GTT GGA 3' (SEQ ID NO: 19) |
| | | | d | nanoKAZ-3C/XbaI | 5' gcc TCT AGA TTA GGC CAG GAT TCT CTC GCA CAG TCT 3' (SEQ ID NO: 25) |
| K124Q | 1st PCR | pcDNA3-GLsp-WNanoKAZ | a | KAZ-8N/EcoRI | 5' gcg GAA TTC TTT ACG TTG GCA GAT TTC GTT GGA 3' (SEQ ID NO: 19) |
| | | | b | nanoKAZ: K124Q-R | 5' GGT GAC GGT GAT CTG CTT GCC GTC GAA 3' (SEQ ID NO: 27) |
| | | pcDNA3-GLsp-WNanoKAZ | c | nanoKAZ: K124Q-F | 5' TTC GAC GGC AAG CAG ATC ACC GTC ACC 3' (SEQ ID NO: 28) |
| | | | d | BGH-R | 5' TAG AAG GCA CAG TCC AGG 3' (SEQ ID NO: 29) |
| | 2nd PCR | 1st PCR product | a | KAZ-8N/EcoRI | 5' gcg GAA TTC TTT ACG TTG GCA GAT TTC GTT GGA 3' (SEQ ID NO: 19) |
| | | | d | nanoKAZ-3C/XbaI | 5' gcc TCT AGA TTA GGC CAG GAT TCT CTC GCA CAG TCT 3' (SEQ ID NO: 25) |
| I138Y | 1st PCR | pcDNA3-GLsp-WNanoKAZ | a | KAZ-8N/EcoRI | 5' gcg GAA TTC TTT ACG TTG GCA GAT TTC GTT GGA 3' (SEQ ID NO: 19) |
| | | | b | nanoKAZ: I138Y-R | 5' CAG TCT CTC GTC ATA GAT CTT GTT GCC 3' (SEQ ID NO: 30) |
| | | pcDNA3-GLsp-WNanoKAZ | c | nanoKAZ: I138Y-F | 5' GGC AAC AAG ATC TAT GAC GAG AGA CTG 3' (SEQ ID NO: 31) |
| | | | d | BGH-R | 5' TAG AAG GCA CAG TCC AGG 3' (SEQ ID NO: 29) |
| | 2nd PCR | 1st PCR product | a | KAZ-8N/EcoRI | 5' gcg GAA TTC TTT ACG TTG GCA GAT TTC GTT GGA 3' (SEQ ID NO: 19) |
| | | | d | BGH-R | 5' TAG AAG GCA CAG TCC AGG 3' (SEQ ID NO: 29) |
| R166N | PCR | pcDNA3-GLsp-WNanoKAZ | a | nanoKAZ-4F | 5' gcc GTC GAC GAC CAC CAC TTC AAG GTC ATC CTG CAC T 3' (SEQ ID NO: 32) |
| | | | b | nanoKAZ: R166N-R | 5' gcc TCT AGA TTA GGC CAG GAT GTT CTC GCA CAG TCT 3' (SEQ ID NO: 33) |

Example 8: Construction of E. coli Expression Vectors for ZZ-Fused Single Amino Acid-Substituted WNanoKAZ Mutants To express as soluble proteins, single amino acid-substituted WNanoKAZ mutant genes were fused to ZZ domain to construct expression vectors. Specifically, pCold-ZZ-X (described in Inouye & Sahara, Protein Express. Purif. (2009) 66: 52-57) was used. The DNA fragment obtained in EXAMPLE 7 was digested with the restriction enzymes of EcoRI and XbaI and ligated to the EcoRI-XbaI site of the expression vector to construct the following 5 expression vectors capable of expressing the ZZ domain-fused single amino acid-substituted WNanoKAZ mutants: pCold-ZZ-P-WNanoKAZ-V90I, pCold-ZZ-P-WNanoKAZ-E115P, pCold-ZZ-P-WNanoKAZ-K124Q, pCold-ZZ-P-WNanoKAZ-I138Y and pCold-ZZ-P-WNanoKAZ-R166N. The nucleotide sequence of the inserted DNA was confirmed by sequencing using a DNA Sequencer (manufactured by ABI Inc.).

The substituted amino acids and nucleotides in the amino acid sequence of WNanoKAZ mutant are shown in TABLE 5

TABLE 5

Substituted amino acids and nucleotides in WNanoKAZ mutants

| WNanoKAZ mutant (WNanoKAZ-) | Nucleotide sequence | |
|---|---|---|
| | Substitution (before) | Substitution (after) |
| V90I | 268 GTC(V) | 268 ATT(I) |
| E115P | 343 GAG(E) | 343 CCT(P) |
| K124Q | 370 AAG(K) | 370 CAG(Q) |
| I138Y | 412 ATC(I) | 412 TAT(Y) |
| R166N | 496 AGA(R) | 496 AAC(N) |

Example 9: Expression of ZZ-Fused KAZ Mutants in E. coli and Preparation of Crude Enzyme Solution In order to express ZZ-fused KAZ mutants in E. coli, the recombinant plasmid produced in EXAMPLE 8 and pCold-ZZ-P-WNanoKAZ produced in EXAMPLE 1 were used. The crude enzyme solution was prepared in a manner similar to EXAMPLE 2, using the E. coli BL21 strain (Novagen, Madison, Wis.) as a host cell. Then, 5 µL of the crude enzyme solution obtained was subjected to SDS-PAGE analysis to confirm the protein expression in all mutants. The results are shown in FIG. 1. In FIG. 1, M and 1 to 8 represent as follows. M: molecular weight size markers; 1: ZZ-P-KAZ; 2: ZZ-P-WNanoKAZ; 3: ZZ-P-WNanoKAZ-V90I; 4: ZZ-P-WNanoKAZ-E115P; 5: ZZ-P-WNanoKAZ-K124Q; 6: ZZ-P-WNanoKAZ-I138Y; 7: ZZ-P-WNanoKAZ-R166N; 8: ZZ-P-dnKAZ. It was confirmed from FIG. 1 that all mutants were expressed.

Example 10: Assay for Luminescence Activity of ZZ-Fused WNanoKAZ Mutants in Crude Enzyme Solution DTT was added to the crude enzyme solution obtained in EXAMPLE 9 at a final concentration of 1 mM, and then allowed to stand in an ice-water bath over 8 hours or more. After 1 µL of the crude enzyme solution was added to 100 µL of 30 mM Tris-HCl (pH 7.6)-10 mM EDTA (Wako Pure Chemical Industries, Ltd.) containing 1 µg of coelenterazine (manufactured by JNC Corp.), a luminescence reaction was started. Luminescence activity was measured for 60 seconds using a luminometer (manufactured by Atto Inc.: AB2200). The maximum intensity of luminescence ($I_{max}$) was given as a relative luminescence activity (rlu).

The results reveal that WNanoKAZ, WNanoKAZ-I90V, WNanoKAZ-E115P, WNanoKAZ-K124Q, WNanoKAZ-I138Y and WNanoKAZ-R166N showed 64-fold, 34-fold, 31-fold, 34-fold, 8.5-fold and 32-fold higher activity, respectively, than native KAZ.

Also, WNanoKAZ, WNanoKAZ-I90V, WNanoKAZ-E115P, WNanoKAZ-K124Q, WNanoKAZ-I138Y and WNanoKAZ-R166N showed 8.6-fold, 4.6-fold, 4.2-fold, 4.6-fold, 1.1-fold and 4.3-fold higher activity, respectively, than the relative activity 7.4 of dnKAZ.

The activity of WNanoKAZ-I138Y decreased to the same level as that of dnKAZ, clearly showing that the substitution of isoleucine for tyrosine at amino acid position 138 was critical for enhancing the activity of KAZ.

These results revealed that the substitution of Y138I in the 5 amino acid substitutions was critical and the higher activity could be achieved by at least 3 substitutions out of the remaining 4 substitutions, and preferably 4 substitutions, as shown in TABLE 6.

TABLE 6

Luminescence activity of ZZ-fused WNanoKAZ mutants in crude enzyme solution

| Expression vector (pCold-ZZ-P-) | Relative luminescence activity ($I_{max}$) |
|---|---|
| KAZ | 1.0 |
| WNanoKAZ | 64 |
| WNanoKAZ-I90V | 34 |
| WNanoKAZ-E115P | 31 |
| WNanoKAZ-K124Q | 34 |
| WNanoKAZ-I138Y | 8.5 |
| WNanoKAZ-R166N | 32 |
| dnKAZ | 7.4 |

Example 11: Substrate Specificity of WNanoKAZ Mutants

Each of the coelenterazine analogues used for substrate specificity studies was synthesized by the methods described in publications. Specifically, bis-coelenterazine was synthesized by the method described in Nakamura et al. (1997) Tetrahedron Lett. 38: 6405-6406, furimazine by the method described in Hall et al. (2012) ACS Chem. Biol. 16; 848-1857, and, 6h-coelenterazine, f-coelenterazine and 6h-f-coelenterazine by the method described in Inouye et al (2013) Biochem. Biophys. Res. Commun. 437: 23-28. Luminescence activity was measured by the same method as in EXAMPLE 10, using the crude enzyme solution obtained in EXAMPLE 10, in which coelenterazine or its analogue was used as the luminescence substrate.

As a result, WNanoKAZ and its single amino acid-substituted mutants exhibited enhanced luminescence activity, namely, WNanoKAZ, WNanoKAZ-I90V, WNanoKAZ-E115P, WNanoKAZ-K124Q, WNanoKAZ-I138Y and WNanoKAZ-R166N exhibited 8.6-fold, 4.6-fold, 4.2-fold, 4.6-fold, 1.1-fold and 4.3-fold higher activity, respectively, than the other coelenterazine analogues when coelenterazine was used as the substrate, as shown in TABLE 7. It is noted from TABLE 7 that even when h-coelenterazine was used as the substrate, WNanoKAZ and its single amino acid-substituted mutants showed the activity as high as in the case when coelenterazine was used as the substrate.

TABLE 7

Substrate specificity of WNanoKAZ mutants

| WNanoKAZ mutants | CTZ $I_{max}$ | CTZ Int. | h-CTZ $I_{max}$ | h-CTZ Int. | 6h-CTZ $I_{max}$ | 6h-CTZ Int. | bis-CTZ $I_{max}$ | bis-CTZ Int. | f-CTZ $I_{max}$ | f-CTZ Int. | 6h-f-CTZ $I_{max}$ | 6h-f-CTZ Int. | Furimazine $I_{max}$ | Furimazine Int. |
|---|---|---|---|---|---|---|---|---|---|---|---|---|---|---|
| KAZ | 1.0 | 1.0 | 1.2 | 0.9 | 0.08 | 0.1 | 0.5 | 0.1 | 1.0 | 0.9 | 0.3 | 0.4 | 0.2 | 0.3 |
| WNanoKAZ | 64 | 56 | 64 | 33 | 8.9 | 7.5 | 32 | 24 | 48 | 32 | 41 | 34 | 26 | 29 |
| WNanoKAZ-V90I | 34 | 35 | 41 | 22 | 5.1 | 5.6 | 23 | 21 | 31 | 22 | 23 | 23 | 17 | 15 |
| WNanoKAZ-E115P | 31 | 26 | 27 | 17 | 5.9 | 6.1 | 18 | 19 | 22 | 14 | 14 | 11 | 13 | 11 |
| WNanoKAZ-K124Q | 34 | 32 | 70 | 41 | 6.2 | 6.1 | 36 | 33 | 64 | 40 | 40 | 35 | 18 | 11 |
| WNanoKAZ-I138Y | 8.5 | 8.9 | 35 | 22 | 1.7 | 2.8 | 18 | 17 | 29 | 18 | 17 | 10 | 11 | 8.9 |
| WNanoKAZ-R166N | 32 | 36 | 43 | 28 | 4.6 | 6.1 | 17 | 18 | 38 | 27 | 13 | 8.8 | 17 | 12 |
| dnKAZ (16mutants) | 7.4 | 7.1 | 129 | 92 | 5.3 | 4.9 | 98 | 93 | 136 | 91 | 80 | 67 | 47 | 43 |

Example 12: Secretory Expression Vectors for WNanoKAZ Mutants Using the Secretory Signal Peptide Sequence of *Gaussia* Luciferase Secretory expression vectors for WNanoKAZ mutants were constructed as follows, using the secretory signal peptide sequence of *Gaussia* luciferase. The WNanoKAZ mutant gene fragment prepared in EXAMPLE 7 using the pcDNA3-GLsp-vector obtained in EXAMPLE 4 was digested with the restriction enzymes of EcoRI/XbaI in a conventional manner and ligated to the EcoRI-XbaI site of pcDNA3-GLsp to construct the following expression vectors: pcDNA3-GLsp-WNanoKAZ-V90I, pcDNA3-GLsp-WNanoKAZ-E115P, pcDNA3-GLsp-WNanoKAZ-K124Q, pcDNA3-GLsp-WNanoKAZ-I138Y and pcDNA3-GLsp-WNanoKAZ-R166N. The gene sequence inserted was confirmed by sequencing using a DNA Sequencer (manufactured by ABI Inc.).

Example 13: Transfection of Vectors into Animal Culture Cells and Preparation of Enzyme for Assay (1) Purification of Expression Plasmid The recombinant plasmid obtained in EXAMPLE 12 or 4 was purified in a manner similar to EXAMPLE 5 and dissolved in sterile water. The firefly luciferase vector (pGL4.13 [Luc2/sv40]: manufactured by Promega Corp.) was similarly prepared and used as an internal standard.

(2) Transfection and Preparation of Enzyme for Assay

Culture medium containing two amino acid-substituted KAZ mutants and three amino acid-substituted KAZ mutants and cell extracts of the KAZ mutants as the enzyme solutions were prepared by the same procedure as in EXAMPLE 9.

The resultant culture medium and cell extracts were used to measure luminescence activity as in EXAMPLE 6. As shown in TABLE 8, it was not recognized that WNanoKAZ and WNanoKAZ mutants happened to secret from the cells, as opposed to dnKAZ, while the mutants were expressed in the cytoplasm.

TABLE 8

Luminescence activity of WNanoKAZ mutants expressed by secretory expression vectors for WNanoKAZ using the secretory signal peptide sequence of *Gaussia* luciferase

| Expression vector (pcDNA3-GLsp-) | Relative luminescence activity (%, $I_{max}$) Culture medium | Relative luminescence activity (%, $I_{max}$) Cell extracts |
|---|---|---|
| KAZ | 0.1 | 0.2 |
| WNanoKAZ | <0.01 | 22 |
| WNanoKAZ-I90V | 0.03 | 15 |
| WNanoKAZ-E115P | <0.01 | 12 |
| WNanoKAZ-K124Q | 0.03 | 21 |
| WNanoKAZ-I138Y | <0.01 | 10 |
| WNanoKAZ-R166N | <0.01 | 26 |
| dnKAZ | 100$^a$ | 16 |

These results demonstrate that the chimeric protein of KAZ and nanoKAZ, in which 5 amino acids were substituted, showed higher luminescence activity than native KAZ when coelenterazine was used as the substrate. The results reveal that the substitution of isoleucine at position of 138 was critical for the enhanced activity and, in the remaining 4 substitutions, at least 3 substitutions, preferably 4 substitutions are associated with the enhanced activity. In addition, these chimeric proteins have the property that into aminal culture cells and advantageously used for reporter assay in the cytoplasm, and the like.

It had been observed by preliminary experiments for the present invention that a mutant with substitution of valine, not with isoleucine, for tyrosine at amino acid position 138 gave the same results as with the isoleucine substitution in the same experiments as demonstrated in EXAMPLES above. The results from a series of experiments of the present invention reveal that not only the substitution of isoleucine but also the substitution of valine for tyrosine at position of 138 can provide the mutants of the invention with the enhanced luminescence activity.

SEQUENCE LISTING FREE TEXT

[SEQ ID NO: 1] Nucleotide sequence of KAZ.
[SEQ ID NO: 2] Amino acid sequence of KAZ.
[SEQ ID NO: 3] Nucleotide sequence of nanoKAZ.
[SEQ ID NO: 4] Amino acid sequence of nanoKAZ.
[SEQ ID NO: 5] Nucleotide sequence of WNanoKAZ.

[SEQ ID NO: 6] Amino acid sequence of WNanoKAZ.
[SEQ ID NO: 7] Nucleotide sequence of WNanoKAZ-I90V.
[SEQ ID NO: 8] Amino acid sequence of WNanoKAZ-I90V.
[SEQ ID NO: 9] Nucleotide sequence of WNanoKAZ-E115P.
[SEQ ID NO: 10] Amino acid sequence of WNanoKAZ-E115P.
[SEQ ID NO: 11] Nucleotide sequence of WNanoKAZ-K124Q.
[SEQ ID NO: 12] Amino acid sequence of WNanoKAZ-K124Q.
[SEQ ID NO: 13] Nucleotide sequence of WNanoKAZ-I138Y.
[SEQ ID NO: 14] Amino acid sequence of WNanoKAZ-I138Y.
[SEQ ID NO: 15] Nucleotide sequence of WNanoKAZ-R166N.
[SEQ ID NO: 16] Amino acid sequence of WNanoKAZ-R166N.
[SEQ ID NO: 17] Nucleotide sequence of dnKAZ.
[SEQ ID NO: 18] Amino acid sequence of dnKAZ.
[SEQ ID NO: 19] Nucleotide sequence of the primer used in EXAMPLES (KAZ-8N/EcoRI).
[SEQ ID NO: 20] Nucleotide sequence of the primer used in EXAMPLES (KAZ-31/SalI247-R).
[SEQ ID NO: 21] Nucleotide sequence of the primer used in EXAMPLES (GLsp-1R/EcoRI).
[SEQ ID NO: 22] Nucleotide sequence of the primer used in EXAMPLES (T7).
[SEQ ID NO: 23] Nucleotide sequence of the primer used in EXAMPLES (nanoKAZ:E115P-R).
[SEQ ID NO: 24] Nucleotide sequence of the primer used in EXAMPLES (nanoKAZ:E115P-F).
[SEQ ID NO: 25] Nucleotide sequence of the primer used in EXAMPLES (nanoKAZ-3C/XbaI).
[SEQ ID NO: 26] Nucleotide sequence of the primer used in EXAMPLES (nanoKAZ:V90I-F).
[SEQ ID NO: 27] Nucleotide sequence of the primer used in EXAMPLES (nanoKAZ:K124Q-R).
[SEQ ID NO: 28] Nucleotide sequence of the primer used in EXAMPLES (nanoKAZ:K124Q-F).
[SEQ ID NO: 29] Nucleotide sequence of the primer used in EXAMPLES (BGH-R).
[SEQ ID NO: 30] Nucleotide sequence of the primer used in EXAMPLES (nanoKAZ:I138Y-R).
[SEQ ID NO: 31] Nucleotide sequence of the primer used in EXAMPLES (nanoKAZ:I138Y-F).
[SEQ ID NO: 32] Nucleotide sequence of the primer used in EXAMPLES (nanoKAZ-4F).
[SEQ ID NO: 33] Nucleotide sequence of the primer used in EXAMPLES (nanoKAZ:R166N-R).

The invention claimed is:

1. A luciferase mutant selected from (a) or (b) below:
   (a) a luciferase mutant comprising the amino acid sequence of SEQ ID NO: 2 substituted at the positions consisting of:
   (i) tyrosine at the position of 138 and isoleucine at the position of 90; and
   (ii) at least 2 positions selected from the group consisting of proline at the position of 115, glutamine at the position of 124, and asparagine at the position of 166; and wherein the luciferase mutant has luciferase activity; and
   (b) a luciferase mutant comprising the amino acid sequence of SEQ ID NO: 2 substituted at the positions consisting of:
   (i) tyrosine at the position of 138 and isoleucine at the position of 90;
   (ii) at least 2 positions selected from the group consisting of proline at the position of 115, glutamine at the position of 124, and asparagine at the position of 166; and
   (iii) one to sixteen positions other than the positions of 4, 11, 18, 27, 33, 43, 44, 54, 68, 72, and 75, and having a luciferase activity.

2. The luciferase mutant according to claim 1, wherein the luciferase mutant comprises the amino acid sequence of SEQ ID NO: 2 substituted at the positions consisting of:
   (i) tyrosine at the position of 138 and isoleucine at the position of 90;
   (ii) at least 2 positions selected from the group consisting of proline at the position of 115, glutamine at the position of 124, and asparagine at the position of 166; and
   (iii) one to ten positions other than the positions of 4, 11, 18, 27, 33, 43, 44, 54, 68, 72, and 75.

3. The luciferase mutant according to claim 1, wherein the tyrosine at the position 138 is substituted with isoleucine or valine.

4. The luciferase mutant according to claim 1, wherein the luciferase mutant is selected from (c) or (d) below:
   (c) a luciferase mutant comprising the amino acid sequence of SEQ ID NO: 6, SEQ ID NO: 10, SEQ ID NO: 12, or SEQ ID NO: 16; and,
   (d) a luciferase mutant comprising the amino acid sequence of SEQ ID NO: 6, SEQ ID NO: 10, SEQ ID NO: 12, or SEQ ID NO: 16, substituted at one to sixteen positions other than the positions of 4, 11, 18, 27, 33, 43, 44, 54, 68, 72, and 75, of SEQ ID NO: 6, SEQ ID NO: 8, SEQ ID NO: 10, SEQ ID NO: 12, or SEQ ID NO: 16.

5. The luciferase mutant according to claim 4, wherein the luciferase mutant comprises the amino acid sequence of SEQ ID NO: 6, SEQ ID NO: 10, SEQ ID NO: 12, or SEQ ID NO: 16, substituted at one to ten positions other than the positions of 4, 11, 18, 27, 33, 43, 44, 54, 68, 72, and 75, of SEQ ID NO: 6, SEQ ID NO: 10, SEQ ID NO: 12, or SEQ ID NO: 16.

6. A polynucleotide comprising a polynucleotide encoding the luciferase mutant according to claim 1.

7. A recombinant vector comprising the polynucleotide according to claim 6.

8. A transformant transformed with the recombinant vector according to claim 7.

9. A method for producing the luciferase mutant according to claim 1, which comprises the steps of culturing a transformant transformed with a recombinant vector comprising a polynucleotide encoding the luciferase mutant according to claim 1 and producing the luciferase mutant.

10. A kit comprising at least one selected from the luciferase mutant according to claim 1, a polynucleotide encoding the luciferase mutant, a recombinant vector comprising the polynucleotide encoding the luciferase mutant, and a transformant transformed with the recombinant vector comprising the polynucleotide encoding the luciferase mutant.

11. The kit according to claim 10, further comprising a luciferin.

12. The kit according to claim 11, wherein the luciferin is a coelenterazine analogue.

13. The kit according to claim 12, wherein the coelenterazine analogue is coelenterazine or h-coelenterazine.

14. A method for performing a luminescence reaction, which comprises contacting the luciferase mutant according to claim 1 with a luciferin.

15. The method according to claim 14, wherein the luciferin is a coelenterazine analogue.

16. The method according to claim 15, wherein the coelenterazine analogue is coelenterazine or h-coelenterazine.

17. A method for assaying the transcription activity of a promoter-containing polynucleotide sequence, which comprises using a polynucleotide encoding the luciferase mutant according to claim 1 as a reporter gene, wherein the polynucleotide encoding the luciferase mutant is operably fused to the promoter-containing polynucleotide sequence, wherein the luciferase mutant expressed is contacted with a luciferin.

18. The method according to claim 17, wherein the luciferin is a coelenterazine analogue.

19. The method according to claim 18, wherein the coelenterazine analogue is coelenterazine or h-coelenterazine.

* * * * *